(12) United States Patent
Snoeck et al.

(10) Patent No.: US 9,719,067 B2
(45) Date of Patent: *Aug. 1, 2017

(54) GENERATION OF ANTERIOR FOREGUT ENDODERM FROM PLURIPOTENT CELLS

(71) Applicant: Mount Sinai School of Medicine, New York, NY (US)

(72) Inventors: Hans-Willem Snoeck, Brooklyn, NY (US); Michael Green, New York, NY (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/959,800

(22) Filed: Dec. 4, 2015

(65) Prior Publication Data

US 2016/0168535 A1  Jun. 16, 2016

Related U.S. Application Data

(62) Division of application No. 13/643,032, filed as application No. PCT/US2011/033751 on Apr. 25, 2011, now Pat. No. 9,234,170.

(60) Provisional application No. 61/436,166, filed on Jan. 25, 2011, provisional application No. 61/392,429, filed on Oct. 12, 2010, provisional application No. 61/343,272, filed on Apr. 25, 2010.

(51) Int. Cl.
*C12N 5/00* (2006.01)
*C12N 5/073* (2010.01)
*C12N 5/071* (2010.01)
*C12N 5/074* (2010.01)

(52) U.S. Cl.
CPC ......... *C12N 5/0603* (2013.01); *C12N 5/0607* (2013.01); *C12N 5/0617* (2013.01); *C12N 5/0688* (2013.01); *C12N 2501/115* (2013.01); *C12N 2501/117* (2013.01); *C12N 2501/119* (2013.01); *C12N 2501/15* (2013.01); *C12N 2501/155* (2013.01); *C12N 2501/16* (2013.01); *C12N 2501/385* (2013.01); *C12N 2501/40* (2013.01); *C12N 2501/41* (2013.01); *C12N 2501/415* (2013.01); *C12N 2506/02* (2013.01); *C12N 2506/03* (2013.01); *C12N 2506/45* (2013.01)

(58) Field of Classification Search
USPC ......................................................... 435/325
See application file for complete search history.

(56) References Cited

U.S. PATENT DOCUMENTS

| | | | |
|---|---|---|---|
| 4,514,420 A | 4/1985 | Imada et al. | |
| 7,695,963 B2 * | 4/2010 | Agulnick | C12N 5/0603 435/325 |
| 8,268,621 B2 * | 9/2012 | Turovets | C12N 5/0603 435/377 |
| 8,507,274 B2 * | 8/2013 | Melton | C12N 5/0603 435/366 |
| 8,647,873 B2 * | 2/2014 | D'Amour | C12N 5/0603 435/325 |
| 9,005,962 B2 * | 4/2015 | Morrison | C12N 5/0603 435/325 |
| 9,222,069 B2 * | 12/2015 | D'Amour | C12N 5/0603 |
| 2006/0003313 A1 | 1/2006 | D'Amour et al. | |
| 2007/0134744 A1 | 6/2007 | Atadja et al. | |
| 2009/0298169 A1 * | 12/2009 | Dalton | C12N 5/067 435/366 |
| 2010/0272695 A1 * | 10/2010 | Agulnick | C12N 5/0676 424/93.7 |
| 2012/0064050 A1 | 3/2012 | Calle et al. | |
| 2012/0135519 A1 * | 5/2012 | Ameri | C12N 5/067 435/366 |

FOREIGN PATENT DOCUMENTS

| | | | |
|---|---|---|---|
| JP | 2012-527880 | | 11/2012 |
| WO | WO 2010/002846 | * | 1/2010 |
| WO | 2010136583 A2 | | 12/2010 |
| WO | 2011139628 A1 | | 11/2011 |
| WO | 2013106677 A1 | | 7/2013 |

OTHER PUBLICATIONS

Kearns, Stem Cell Res., Nov. 2013, vol. 11, No. 3, p. 1003-1012.*
D'Amour (Nature Biotech., 2005, vol. 23, No. 12, p. 1534-1541).*
Kubo (Development, 2004, vol. 131, p. 1651-1662).*
Gadue (Proc Natl Acad Sci USA, 2006, vol. 103, p. 16806-16811).*
Zorn (Annu. Rev. Cell Dev. Biol. 2009, vol. 25, p. 221-251).*
Pera (J. Cell Science, 2004, vol. 117, p. 1269-1280).*
Green (Nat. Biotechnol., 2011, 29(3): 267-72).*
Tada (Development, vol. 2005, vol. 132, p. 4363-4374).*
Wood (Mechanisms of Develop., 1999, vol. 86, p. 192-201).*
Gouon-Evans (Nat Biotechnol, 2006, vol. 24, p. 1402-1411).*
Ameri, J., "FGF Signalling in specification of hESC-derived definitive endoderm," Stem Cell Center, Faculty of Medicine, Lund University, Sweden, Doctoral Dissertation, 2010, pp. 1-91.
Ameri, J., et al., "FGF2 specifies hESC-derived definitive endoderm into foregut/midgut cell lineages in concentration-dependent manner," Stem Cells, 2010, pp. 45-56, vol. 28, No. 1.
Biver, E, et al., "Fibroblast growth factor 2 inhibits up-regulation of bone morphogenic proteins and their receptors during osteoblastic differentiation of human mesenchymal stem cells", Biochem Biophys Res Commun, Nov. 2012, pp. 737-742, vol. 427, No. 4, Publisher: Elsevier, Published in: http://www.ncbi.nlm.nih.gov/pubmed/23044416.

(Continued)

*Primary Examiner* — Michael Wilson
(74) *Attorney, Agent, or Firm* — Judith A. Evans; Timothy H. Van Dyke; Beusse Wolter Sanks & Maire

(57) ABSTRACT

The invention is directed to in vitro methods of inducing differentiation of anterior foregut endoderm and the enriched populations of anterior foregut endoderm produced by such methods. Such enriched populations are useful for studies of the molecular events that occur during differentiation and for generating cells for cell replacement therapy.

13 Claims, 14 Drawing Sheets

(56) References Cited

OTHER PUBLICATIONS

D'Amour, K., et al., "Production of pancreatic hormone-expressing endocrine cells from human embryonic stem cells", Nature Biotechnology, Jan. 1, 2006, pp. 1392-1401, vol. 24, No. 11, Publisher: Nature Publishing Group, Published in: http://www.ncbi.nlm.nih.gov/pubmed/17053790.
Gadue, P., et al., "Wnt and TGF-beta signaling are required for the induction of an in vitro model of primitive streak formation using embryonic stem cells", Proceedings of the National Academy of Sciences in the United States of America, Nov. 2006, pp. 16806-16811, vol. 103, No. 45, Publisher: National Academy of Sciences, Published in: http://www.ncbi.nlm.nih.gov/pubmed/?term=Wnt+and+TGF-beta+signaling+are+required+for+the+induction+of+an+in+vitro+model+of+primitive+streak+formation+.
Green, M., et al., "Novel approaches for immune reconstitution and adaptive immune modeling with human pluripotent stem cells", BMC Medicine, May 10, 2011, pp. 1-5, vol. 9, No. 1, Publisher: Biomed Central Ltd., Published in: http://www.ncbi.nlm.nih.gov/pubmed/?term=Novel+approaches+for+immune+reconstitution+and+adaptive+immune+modeling+with+human+pluripotent+st.
Green, M., et al., "Generation of anterior foregut endoderm from human embryonic and induced pluripotent stem cells," Nat Biotechnol, 2011, pp. 267-272, vol. 29, No. 3.
Halder, S., et al., "A Specific Inhibitor of TGF-B Receptor Kinase, SB-431542, as a Potent Antitumor for Human Cancers," Neoplasia, 2005, pp. 509-521, vol. 7, No. 5.
Kadzik, R., et al., "Directing Lung Endoderm Differentiation in Pluripotent Stem Cells", Cell Stem Cell, Apr. 2012, pp. 355-361, vol. 10, No. 4, Publisher: Cell Press, Published in: http://www.ncbi.nlm.nih.gov/pubmed/22482501.
Kearns, N., et al. "Generation of organized anterior foregut epithelia from pluripotent stem cells using small molecules", Stem Cell Research, Nov. 2013, pp. 1003-1012, vol. 11, No. 3, Publisher: Elsevier, Published in: http://www.ncbi.nlm.nih.gov/pubmed/?term=Generation+of+organized+anterior+foregut+epithelia+from+pluripotent+stem+cells+using+small+molecules.
Liu, Y., et al., "Function of TGF-beta and p38 MAKP signaling pathway in osteoblast differentiation from rat adipose-derived stem cells", European Review for Medical and Pharmacological Sciences, Jun. 2013, pp. 1611-1619, vol. 17, No. 12, Published in: http://www.ncbi.nlm.nih.gov/pubmed/?term=Function+of+TFG-beta+and+p38+MAKP+signaling+pathway+in+osteoblast+differentiation+from+rat+adipose-de.
Longmire, T., et al., "Efficient Derivation of Purified Lung and Thyroid Progenitors from Embryonic Stem Cells", Cell Stem Cell, 2012, pp. 398-411, vol. 10, No. 4, Publisher: Cell Press, Published in: http://www.ncbi.nlm.nih.gov/pubmed/?term=Efficient+Derivation+of+Purified+Lung+and+Thyroid+Progenitors+from+Embryonic+Stem+Cells.
Morrisey, E., et al., "Preparing for the first breath: genetic and cellular mechansims in lung development," Dev Cell, 2010, pp. 8-23, vol. 18, No. 1.
Papetti, M., et al., "FGF-2 antagnoizes the TGF-beta1-mediated induction of pericyte alpha-smooth muscle actin expression: A role for Myf-5 and Smad-mediated signaling pathways", Invest Ophthalmol Vis Sci, Nov. 2003, pp. 4994-5005, vol. 44, No. 11, Publisher: Association for Research in Vision and Ophthalmology, Published in: http://www.ncbi.nlm.nih.gov/pubmed/14578427.
Que, J., et al., "Multiple Dose-Dependent Roles for Sox2 in the Patterning and Differentiation of Anterior Foregut Endoderm", Development, Jul. 2007, pp. 2521-2531, vol. 134, No. 13, Publisher: Cambridge, Published in: http://www.ncbi.nlm.nih.gov/pmc/articles/PMC3625644/.

Sulzbacher, S., et al., "Activin A-Induced Differentiation of Embryonic Stem Cells into Endoderm and Pancreatic Progenitors—The Influence of Differentiation Factors and Culture Conditions", Stem Cell Reviews and Reports, Jun. 1, 2009, pp. 159-173, vol. 5, No. 2, Publisher: Springer, Published in: http://www.ncbi.nlm.nih.gov/pubmed/19263252.
Zhu, F., et al., "Generation of pancreatic insulin-producing cells from rhesus monkey induced pluripotent stem cells", Diabetologia, Jul. 14, 2011, pp. 2325-2336, vol. 54, No. 9, Publisher: Springer, Published in: http://www.ncbi.nlm.nih.gov/pubmed/?term=Generation+of+pancreatic+insulin-producing+cells+from+rhesus+monkey+induced+pluripotent+stem+cells.
Zorn, A., et al., "Vertebrate Endoderm Development and Organ Formation", Vertebrate Endoderm Development and Organ Formation, 2009, pp. 221-251, vol. 25, Publisher: Annual Reviews, Published in: http://www.ncbi.nlm.nih.gov/pubmed/19575677.
EPO, Extended European Search Report, European Patent App. 11777870, issued on Oct. 28, 2013, pp. 1-6.
JPO, Notice of Reasons for Refusal, Japanese Patent App. No. 2013-508123, issued on Mar. 30, 2015, pp. 1-4.
SIPO, Notification of First Office Action, Chinese Patent App. No. 201180031569.9, issued on Nov. 7, 2013, pp. 1-6.
SIPO, Notification of Third Office Action, Chinese Patent App. No. 201180031569.9, issued on Jan. 23, 2015, pp. 1-6.
Chambers, S., et al., "Highly efficient neural conversion of human ES and iPS cells by dual inhibition of SMAD signaling", Nature Biotechnology, Mar. 1, 2009, pp. 275-280, vol. 27, No. 3, Publisher: Nature Publishing Group, Published in: http://www.ncbi.nlm.nih.gov/pubmed/?term=Highly+efficient+neural+conversion+of+human+ES+and+iPS+cells+by+dual+inhibition+of+SMAD+signaling.
Banerjee, E., et al., "Human Embroynic Stem Cells Differentiated to Lung Lineage-Specific Ameliorate Pulmonary Fibrosis in a Xenograft Transplant Mouse Model," PLoS ONE, Mar. 2012, pp. 1-15, vol. 7, Issue 3.
Kim, K, et al., "Alveolar Epithelial Cell Mesenchymal Transition Develops in Vivo During Pulmonary Fibrosis and is Regulated by the Extracellular Matrix", Proc Natl Acad Sci, Aug. 29, 2006, pp. 13180-13185, vol. 103, No. 35, Publisher: Pnas, Published in: http://www.ncbi.nlm.nih.gov/pubmed/16924102.
Mou, H., et al. "Generation of Multipotent Lung and Airway Progenitors from Mouse ESCs and Patient-Specific Cystic Fibrosis iPSCs," Cell Stem Cell, 2012, pp. 385-397, vol. 10, Publisher: Elsevier Inc.
Seo, E., et al., "Distinct Functions of Sox2 Control Self-Renewal and Differentiation of Osteoblast Lineage", Nov. 2011, pp. 4593-4608, vol. 31, No. 22, Publisher: Molecular Cell Biology, Published in: http://www.ncbi.nlm.nih.gov/pubmed/21930787.
Tompkins, D., et al., "Sox2 is Required for Maintenance and Differentiation of Bronchiolar Clara, Ciliated, and Goblet Cells", Dec. 14, 2009, pp. 1-12, vol. 4, No. 12, Publisher: PLos One, Published in: http://www.ncbi.nlm.nih.gov/pubmed/20011520.
Van Haute, L., et al., "Generation of lung epithelial-like tissue from human embryonic stem cells," Respiratory Research, 2009, pp. 1-10, vol. 10.
Yu, W., et al., "Formation of Cysts by Alveolar Type II Cells in Three-Dimensional Culture Reveals a Novel Mechanism for Epithelial Morphogenesis", May 2007, pp. 1693-1700, vol. 18, Publisher: Molecular Biology of the Cell, Published in: http://www.ncbi.nlm.nih.gov/pubmed/17332496.
EPO, Examination Report, European Patent App. 11 77 7870, issued on Feb. 12, 2016, pp. 1-5.
SIPO, Notification of Second Office Action, Chinese Patent App. No. 201180031569.9, issued on Jul. 21, 2014, pp. 1-5.
ISA/US, International Search Report and Written Opinion, International Patent Application No. PCT/US2013/51913, Issued on Nov. 29, 2013, pp. 1-14.

\* cited by examiner

SEQUENCE LISTING

<160> NUMBER OF SEQ ID NOS: 38

<210> SEQ ID NO 1
<211> LENGTH: 24
<212> TYPE: DNA
<213> ORGANISM: Artificial Sequence
<220> FEATURE:

```
<223> OTHER INFORMATION: Synthetic oligonucleotide: F-Sox2
      recombineering primer

<400> SEQUENCE: 1
gcacatgaag gagcacccgg atta                                              24

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide: R-Sox2
      recombineering primer

<400> SEQUENCE: 2
cgggcagcgt gtacttatcc ttctt                                             25

<210> SEQ ID NO 3
<211> LENGTH: 28
<212> TYPE: DNA
<213> ORGANISM: Artificial Sequence
<220> FEATURE:
<223> OTHER INFORMATION: Synthetic oligonucleotide: F-GCM2
      recombineering primer

<400> SEQUENCE: 3
cagagtgggt cccttcttta cctacaac                                          28

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide: R-GCM2
      recombineering primer

<400> SEQUENCE: 4
tgcctttcac atttccctgc ct                                                22

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide: F-Pax1
      recombineering primer

<400> SEQUENCE: 5
ttagactgcc gtaccctcct cacaa                                             25

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide: R-PAX1
      recombineering primer

<400> SEQUENCE: 6
aggaagggaa agagaaaggg aaggga                                            26

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide: F-SFTPC
``` recombineering primer

<400> SEQUENCE: 7
ccttcttatc gtggtggtgg tggt                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide: R-SFTPC
      recombineering primer

<400> SEQUENCE: 8
tctccgtgtg tttctggctc atgt                                          24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide: F-ACTB
      recombineering primer

<400> SEQUENCE: 9
taagtcctgc cctcatttcc ctct                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide: R-ACTB
      recombineering primer

<400> SEQUENCE: 10
tttgcggatg tccacgtcac actt                                          24

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide: F-GATA6
      recombineering primer

<400> SEQUENCE: 11
agttcctacg cttcgcatcc cttc                                          24

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide: R-GATA6
      recombineering primer

<400> SEQUENCE: 12
tgaacagcag caagtcctcc ca                                            22

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide: F-TBX1
      recombineering primer

<400> SEQUENCE: 13
cggctcctac gactattgcc c                                              21

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide: R-TBX1
      recombineering primer

<400> SEQUENCE: 14
ggaacgtatt ccttgcttgc cct                                            23

<210> SEQ ID NO 15
<211> LENGTH: 27
<212> TYPE: DNA
<213> ORGANISM: Artificial Sequence
<220> FEATURE:
<223> OTHER INFORMATION: Synthetic oligonucleotide: F-SOX17
      recombineering primer

<400> SEQUENCE: 15
ctgttgaatc ataagcttga cctgccc                                        27

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide: R-SOX17
      recombineering primer

<400> SEQUENCE: 16
atcttaaacc cagcgatgct tgcc                                           24

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide: F-PAX6
      recombineering primer

<400> SEQUENCE: 17
gggatgagga tgcattgtgg ttgt                                           24

<210> SEQ ID NO 18
<211> LENGTH: 29
<212> TYPE: DNA
<213> ORGANISM: Artificial Sequence
<220> FEATURE:
<223> OTHER INFORMATION: Synthetic oligonucleotide: R-PAX6
      recombineering primer

<400> SEQUENCE: 18
gaggaagaag agggagaaga aggaagagg                                      29

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide: F-PAX9
      recombineering primer

```
<400> SEQUENCE: 19
tggttatgtt gctggacatg ggtg                                              24

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide: R-PAX9
      recombineering primer

<400> SEQUENCE: 20
ggaagccgtg acagaatgac tacct                                             25

<210> SEQ ID NO 21
<211> LENGTH: 26
<212> TYPE: DNA
<213> ORGANISM: Artificial Sequence
<220> FEATURE:
<223> OTHER INFORMATION: Synthetic oligonucleotide: F-CDX2
      recombineering primer

<400> SEQUENCE: 21
taaatgccag agccaacctg acttcc                                            26

<210> SEQ ID NO 22
<211> LENGTH: 28
<212> TYPE: DNA
<213> ORGANISM: Artificial Sequence
<220> FEATURE:
<223> OTHER INFORMATION: Synthetic oligonucleotide: R-CDX2
      recombineering primer

<400> SEQUENCE: 22
cagcagcaac aacaacacac aaactccc                                          28

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide: F-FOXP2
      recombineering primer

<400> SEQUENCE: 23
tcagcaaatg cagcagatcc ttcag                                             25

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide: R-FOXP2
      recombineering primer

<400> SEQUENCE: 24
acagcctgct gttgttggag aag                                               23

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide: F-MIXL1
      recombineering primer

<400> SEQUENCE: 25
```

```
ctgtgctcct ggaactgaaa cgaa                                          24
```

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide: R-MIXL1
      recombineering primer

<400> SEQUENCE: 26

```
tgaccttggg acctagagtc agagatg                                       27
```

<210> SEQ ID NO 27
<211> LENGTH: 26
<212> TYPE: DNA
<213> ORGANISM: Artificial Sequence
<220> FEATURE:
<223> OTHER INFORMATION: Synthetic oligonucleotide: F-BRACHYURY
      recombineering primer

<400> SEQUENCE: 27

```
cagtggcagt ctcaggttaa gaagga                                        26
```

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide: R-BRACHYURY
      recombineering primer

<400> SEQUENCE: 28

```
cgctactgca ggtgtgagca a                                             21
```

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide: F-NXK2.5
      recombineering primer

<400> SEQUENCE: 29

```
tggagaagac agaggcggac aa                                            22
```

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide: R-NXK2.5
      recombineering primer

<400> SEQUENCE: 30

```
atagacctgc gcctgcgaga a                                             21
```

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide: F-NKX2.1
      recombineering primer

<400> SEQUENCE: 31
cggcatgaac atgagcggca t                                              21

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide: R-NXK2.1
      recombineering primer

<400> SEQUENCE: 32
gccgacaggt acttctgttg cttg                                           24

<210> SEQ ID NO 33
<211> LENGTH: 26
<212> TYPE: DNA
<213> ORGANISM: Artificial Sequence
<220> FEATURE:
<223> OTHER INFORMATION: Synthetic oligonucleotide: F-ODD1
      recombineering primer

<400> SEQUENCE: 33
cagctcacca actactcctt ccttca                                         26

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide: R-ODD1
      recombineering primer

<400> SEQUENCE: 34
tgcaacgcgc tgaaaccata ca                                             22

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide: F-CREB313
      recombineering primer

<400> SEQUENCE: 35
tctccagaac tttgcacaac gatgc                                          25

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide: R-CREB313
      recombineering primer

<400> SEQUENCE: 36
tcctccgtcg aattggtcag gtt                                            23

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide: F-CEBPA
      recombineering primer

<400> SEQUENCE: 37
agaagtcggt ggacaagaac agca                                           24

```
<210> SEQ ID NO 38
<211> LENGTH: 23
<212> TYPE: DNA
<213> ORGANISM: Artificial Sequence
<220> FEATURE:
<223> OTHER INFORMATION: Synthetic oligonucleotide:  R-CEBPA
      recombineering primer

<400> SEQUENCE: 38
attgtcactg gtcagctcca gca                                              23
```

GENERATION OF ANTERIOR FOREGUT ENDODERM FROM PLURIPOTENT CELLS

CLAIM OF PRIORITY

This application is a Divisional application of U.S. National Phase application Ser. No. 13/643,032, filed, Oct. 23, 2012, and claims benefit under 35 U.S.C. §371 of International Patent Application No. PCT/US2011/033751, filed Apr. 25, 2011, and claims benefit of U.S. Provisional Application No. 61/436,166, filed Jan. 25, 2011, U.S. Provisional Application No. 61/392,429, filed Oct. 12, 2010, and U.S. Provisional Application No. 61/343,272, filed Apr. 25, 2010. Each of the aforementioned applications is hereby incorporated by reference herein in its entirety.

GOVERNMENT SPONSORED RESEARCH OR DEVELOPMENT

This invention was made with Government support under Grant No. 5T32CA078207-12 awarded by the National Institutes of Health. The Government has certain rights in the invention.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "IRCU13141_SNOECK_15003-198US4_TB_OW_2016-02-22_SeqListing_ST25.txt" created on Feb. 22, 2016 and is 9 kilobytes in size. The sequence listing contained in this .txt file is part of the specification and is hereby incorporated by reference herein in its entirety.

TECHNICAL FIELD

The present invention relates, at least in part, to methods of generating populations of tissue precursor cells from pluripotent cells, and more particularly to methods of generating anterior foregut endoderm from pluripotent cells.

BACKGROUND

Embryonic stem (ES) cells are pluripotent cells derived from the inner cell mass of the blastocyst and can be maintained in the pluripotent state in defined conditions in both human and mouse. ES cells can theoretically be differentiated into every somatic and germ cell type. The development of appropriate conditions to differentiate ES cells into a variety of cell types and tissues therefore holds major promise for future cell replacement therapy. Pluripotent cells may also be obtained by reprogramming adult somatic cells into a pluripotent state (e.g., induced pluripotent stem cells, or iPS cells), providing a path for the generation of patient-specific pluripotent cells, which would overcome rejection problems associated with transplantation of ES cell-derived tissues.

Development begins with the process of gastrulation, during which undifferentiated cells from the inner cell mass of the blastocyst differentiate into the three germ layers from which all tissues of the body are generated. Ectoderm gives rise to skin and its appendages, the nervous system, and adrenal tissues. Mesoderm develops into the genito-urinary system, connective tissue, muscle, bone, cartilage, blood vessels, blood and heart. Endoderm produces the intestine, liver, pancreas, esophagus, trachea, lung and the pharyngeal apparatus, which is derived from the most anterior foregut endoderm.

Complex patterning processes along the dorsoventral, anteroposterior and left-right axis of the embryo occur, leading to the definition of specific domains in these germ layers that will later on give rise to specific tissues and organs. Patterning is accompanied by complex molecular changes. It therefore appears critical that to obtain enriched or pure and functional populations of mature cells, developmental cues need to be sequentially applied to guide the differentiation of pluripotent cells in vitro.

SUMMARY

At least in part, the present invention is based on the discovery of methods for the generation of anterior foregut endoderm from pluripotent stem cells, e.g., human embryonic and induced pluripotent stem cells.

In certain embodiments, the invention provides a cell population enriched for anterior foregut endoderm cells. In certain embodiments, the invention provides a cell population enriched for pharyngeal endoderm cells. These cell populations can be obtained by the methods described herein. As used herein, the term "cell populations" refers to isolated cell populations, not populations of cells present in an animal as a result of normal development.

In certain embodiments, the invention provides methods for deriving anterior foregut endoderm comprising culturing definitive endoderm with an inhibitor of BMP or an inhibitor of TGF-beta signaling and in the absence of Activin A. In some embodiments, definitive endoderm is cultured with both an inhibitor of BMP and an inhibitor of TGF-beta signaling and in the absence of Activin A.

In preferred embodiments, an inhibitor of BMP is Noggin and an inhibitor of TGF-beta is SB-431542.

In certain embodiments, the invention provides a method of deriving anterior foregut endoderm from pluripotent cells, such as ES cells or iPS cells, comprising inducing said pluripotent cells to form definitive mesoderm, e.g., expressing the markers EPCAM, CXCR4 and C-KIT as set forth herein, and then deriving anterior foregut endoderm from the definitive mesoderm as set forth herein.

In certain embodiments, anterior foregut endoderm cells derived by the methods described herein express FOXA2 and comprise an elevated level of SOX2 expression and a reduced level of CDX2 expression, compared to the expression of SOX2 and CDX2 in definitive endoderm cells.

In a preferred embodiment, the invention provides a method of preparing an enriched population of anterior foregut endoderm cells from pluripotent cells, e.g., ES or iPS cells, most preferably human ES or iPS cells, comprising:

(i) culturing the pluripotent cells in the presence of basic FGF (bFGF), bone morphogenic protein 4 (BMP4) and Activin A to induce said pluripotent cells to form definitive endoderm cells; and (ii) culturing the definitive endoderm cells in the presence of an inhibitor of BMP, e.g., Noggin or Chordin or follistatin, and/or an inhibitor of TGF-beta signaling, e.g., SB-431542, and in the absence of Activin A, to induce the definitive endoderm cells to form anterior foregut endoderm cells.

In certain embodiments, the invention provides a method of identifying an agent that affects the proliferation, differentiation or survival of anterior foregut endoderm cells, comprising culturing an enriched population of anterior foregut endoderm cells in the presence and absence of an agent to be tested and comparing the proliferation, differentiation or survival of said cells in the presence and absence of said agent, wherein a difference in the presence of said agent is indicative of the identification of an agent that affects the proliferation, differentiation or survival of said cells.

In certain embodiments, the invention provides a method of identifying a gene involved in cell differentiation comprising isolating definitive endoderm cells and anterior foregut endoderm cells and comparing the gene expression profiles of said definitive endoderm cells and said anterior foregut endoderm cells, wherein identification of a gene that is differentially expressed between said definitive endoderm cells and said anterior foregut endoderm cells is indicative of a gene involved in cell differentiation.

In certain embodiments, the invention provides a method of identifying an antibody that recognizes a molecular marker of progression from definitive endoderm to anterior foregut endoderm comprising raising antibodies to and enriched population of anterior foregut endoderm cells and screening for an antibody that binds to said anterior foregut endoderm significantly higher than said antibody binds to said definitive endoderm.

In certain embodiments, the invention provides a method of inducing a ventral cell fate in anterior/pharyngeal endoderm or pharyngeal pouch fate, comprising administering one or more factors selected from the group consisting of Wnt ligands, Wnt signaling activators, BMPs, epidermal growth factors (EGFs) and fibroblast growth factors (FGFs).

In certain embodiments, the invention provides a method of inducing a parathyroid fate in a cell by culturing a ventralized anterior foregut endoderm cell with Sonic Hedgehog (SHH) and fibroblast growth factors (FGFs).

In certain embodiments, the invention provides a method of inducing a lung fate in a cell by culturing an anterior foregut endoderm ventralized in the presence of retinoic acid with FGF and Wnt signaling activators.

Also provided are cells and populations of cells (e.g., enriched populations) produced by a method described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
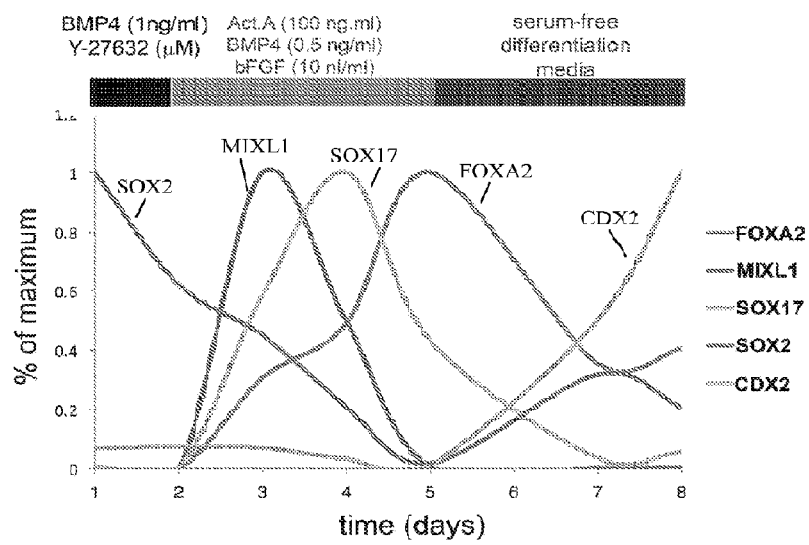
FIGS. 1a-i show induction of AFE markers in NOGGIN/SB-431542-treated definitive endoderm. (1a) Expression of FOXA2, MIXL1, SOX17, SOX2 and CDX2 mRNA during activin Amediated induction of definitive endoderm in hES cells. Data expressed as quantification of mRNA normalized to β-ACTIN (also known as ACTB), scaled proportionally to maximum induction. Cytokines were added as indicated on top of the figure (bar). (1b) Representative flow cytometric analysis of definitive endodermal markers CXCR4, C-KIT and EPCAM at day 5 of activin A induction. Two biologically independent experiments are shown. (1c) Expression of FOXA2, SOX2, CDX2, PAX9 and TBX1 mRNA on day 9 in cultures treated on day 5 after induction of definitive endoderm (see upper left panel), with the factors listed in the lower left panel (n=3 biological replicates; *, significantly different from all other conditions, P<0.0001; one-way ANOVA). d0, prior to start of differentiation; d5, day 5. (1d) Expression of SOX2 and PAX9 on day 9 in cultures treated on day 5, after induction of definitive endoderm, with NOGGIN/SB-431542 (SB) in the presence or absence of sFRP3 (*, P<0.05, n=3 biological replicates). (1e) Expression of BRACHYURY and PAX6 mRNA at day 9 in hES cells differentiated as previously described to neurectoderm (day 1 addition of NOGGIN/SB-431542), or after induction of endoderm (endoderm induction until day 5, followed by addition of NOGGIN/SB-431542). For BRAYCHURY, day 3.5 hES cells exposed to activin A and undergoing gastrulation served as a positive control (*, P<0.0001, n=3 experiments consisting each of three biological replicates). (1f) Expression of ODD1, CDX2, EVX1, CREB313, CEBPA, TBX1, PAX9, SOX2 and FGF8 mRNA in day 9 cultures treated in parallel with either NOGGIN/SB-431542 or cultured in hepatic conditions after induction of definitive endoderm until day 5 (n=3 experiments consisting each of three biological replicates). (1g) Representative flow cytometric analysis of definitive endodermal markers CXCR4 and C-KIT at day 5 of Activin A induction in HDF2 and HDF9 hiPS cells. (1h,i) Expression of FOXA2, SOX2, and PAX9 mRNA in HFGD2 and HDF9 hiPS cells on day 9 in cultures treated from day 5, after induction of definitive endoderm (see upper left panel), with either serum-free differentiation media (ctrl) or NOGGIN/SB-431542 (n=3 biological triplicate replicates, *significantly different from media ctrl).

During embryogenesis, the formation of the anterior and pharyngeal endoderm is a critical step in the establishment of a body plan and in the development of multiple organ systems such as parts of the ear, palatine tonsils, thymus, parathyroids, thyroid, lung, esophagus and trachea. Subsequent to its formation, definitive endoderm differentiates progressively into endoderm sub-lineages. More posterior endoderm gives rise to the midgut and hindgut. The pharyngeal endoderm, anterior to the lung field, forms four outcroppings, called pharyngeal pouches. The respective pouches develop into specific organs, e.g., eustachian tube and inner leaflet of tympanic membrane (1st pouch), palatine tonsils (2nd pouch), thymus (anterior 3rd), parathyroids (dorsal 3rd and 4th pouch), and parafollicular C cells of the thyroid (4th pouch). The thyroid gland proper develops from the floor of the pharynx. Lung, esophagus and trachea are derived from anterior foregut endoderm distal to the pouches. The ability to generate populations of anterior foregut/pharyngeal endoderm cells from pluripotent cells would be useful in cell replacement therapy for these tissues, in assays for agents that affect cell growth and differentiation, and in studies on tissue development and differentiation. There is presently no method, however, for generating populations of anterior foregut endoderm cells from pluripotent cells and the molecular mechanisms that control anterior foregut endoderm formation are poorly defined. It would be advantageous to obtain anterior foregut endoderm cell populations, in order to better understand their formation and tissue development. It has not been possible to date to isolate or generate enriched populations of anterior foregut endoderm cells.

The present invention provides methods for obtaining populations of anterior foregut endoderm by inducing pluripotent cells to differentiate to definitive endoderm, followed by patterning of the definitive endoderm to an anterior fate. Anterior foregut endoderm may subsequently be induced to differentiate into any of the tissues derived therefrom. In certain embodiments, ventral anterior foregut endoderm, parathyroid and lung markers are induced from anterior foregut/pharyngeal endoderm. Thus the present invention provides methods for generating populations of anterior foregut endoderm cells from pluripotent cells. Such cell populations are useful to identify agents that affect cell growth and differentiation, to identify genes involved in tissue development, and to generate differentiated cells and tissues for cell replacement therapies.

As used herein, "anterior foregut endoderm" refers to endoderm that is anterior to the endoderm that gives rise to the liver. One of ordinary skill in the art will readily appreciate that "anterior foregut endoderm" thus includes, for example, pharyngeal endoderm and other, more highly differentiated populations of endodermal cells and that the various cell types encompassed by the term "anterior foregut endoderm" may exhibit different expression patterns of molecular markers. One of ordinary skill in the art will appreciate that "anterior foregut endoderm" gives rise to various tissues, e.g., tonsils, tympanic membrane, thyroid, parathyroid glands, thymus, trachea, esophagus, stomach, lung and larynx/pharynx.

Directed differentiation of pluripotent cells, e.g., ES cells, into definitive endoderm can be obtained by application of high concentrations of Activin A. The scientific basis for this strategy is that signaling by the morphogen nodal is required for endoderm formation. Activin A activates the same receptor as nodal, but is available as a soluble cytokine. Notwithstanding an available method for driving differentiation of ES cells into definitive endoderm, there is currently no method available to anteriorize definitive endoderm in vitro and derive or isolate anterior foregut endoderm.

Embryonic tissues express characteristic sets of molecular markers. Inner cell mass cells express transcription regulators OCT3/4, NANOG, and SOX2. Definitive endoderm cells express transcription regulators FOXA2, SOX17 and FOXA3. Anterior foregut endoderm cells express transcription regulators FOXA2 and SOX2. Pharyngeal endoderm cells express transcription regulators TBX1 and SOX2. Third pharyngeal pouch cells express transcription regulators PAX1/9, HOXA3 and SIX1. Thymic epithelial cells express the transcription regulator FOXN1. The lung field of the anterior foregut endoderm expresses NKX2.1 and GATA6.

The detection of anterior foregut endoderm markers in tissue is not, in and of itself, sufficient to demonstrate the presence of anterior foregut endoderm derived from ES cells. ES cells are maintained in an undifferentiated state under specific culture conditions. Removal of these conditions results in the formation of embryoid bodies (EBs), which are spheres of cells undergoing spontaneous gastrulation, leading to the random generation of derivatives of all germ layers that undergo random differentiation. EBs undergoing random differentiation express markers for many embryonic tissues, including markers for anterior foregut endoderm. Proper classification of ES derived tissues as anterior foregut endoderm thus requires additional characterization of tissue beyond mere expression of markers for anterior foregut endoderm, such as that cell fates not associated with anterior foregut endoderm are suppressed or that definitive endodermal and posterior endodermal signals are depleted is required.

Methods for generating tissue derived from pharyngeal and anterior foregut endoderm may proceed by induction of definitive endoderm from pluripotent cells, induction of definitive endoderm to form anterior foregut endoderm, followed by further differentiation to, e.g., pharyngeal endoderm and specification of specific derivatives.

Generation of Definitive Endoderm

Generation of definitive endoderm from human ES or iPS cells may be accomplished by adapting a protocol used to develop definitive endoderm from mouse ES cells. Kubo et al., Development 131:1651-1662 (2004); Gadue et al., Proc Natl Acad Sci USA 103:16806-16811 (2006); Gouon-Evans et al., Nat Biotechnol, 24:1402-1411 (2006). Human ES cells are pulsed with a low concentration of BMP4 (e.g., about 0.5-10 ng/ml, e.g., 1 ng/ml), cultured in low concentrations of BMP4 and bFGF (e.g., about 5-20 ng/ml, e.g., about 10 ng/ml), and then cultured in a high concentration of Activin A (50-500 ng/ml, e.g., 75-150 ng/ml, e.g., about 100 ng/ml) on non-tissue-treated plastic, resulting in the formation of embryoid bodies (EBs). The EBs consist virtually uniformly of endoderm. Development of endoderm may be confirmed by expression of CXCR4 and c-KIT. Development of endoderm is accompanied by loss of the ES marker, SOX2, and sequential gain of MIXL1, SOX17 and FOXA2, up to day 5.

In some embodiments, other pluripotent stem cells can be used in place of the ES cells. For example, adult stem cells (e.g., adult stem cells obtained from the inner ear, bone marrow, mesenchyme, skin, fat, liver, muscle, or blood of a subject, e.g., the subject to be treated); embryonic stem cells, or stem cells obtained from a placenta or umbilical cord; progenitor cells (e.g., progenitor cells derived from the inner ear, bone marrow, mesenchyme, skin, fat, liver, muscle, or blood); and induced pluripotent stem cells (e.g., iPS cells) can be used. In some embodiments, iPS cells (see, e.g., Maherali and Hochedlinger, Cell Stem Cell 3:595-605 (2008)) are used. In general, cells of human origin are preferred.

Formation of Anterior Foregut Endoderm from Definitive Endoderm

It has been discovered that although Activin A induces endoderm, Activin A posteriorizes this tissue. Preparation of anterior foregut endoderm thus requires reducing or removing Activin A following formation of definitive endoderm. In certain aspects, the present invention thus provides a method for the formation of a population cells enriched for anterior foregut endoderm, and the depletion of mid- and posterior endoderm signals. Such populations express molecular markers that are present in anterior foregut endoderm and are depleted for molecular marker that present not present in anterior foregut endoderm.

Endoderm cell populations are characterized and distinguished by markers known in the art. Within definitive endoderm, the ES marker SOX2 reemerges as a marker of anterior foregut endoderm, while CDX2 is a marker of posterior endoderm (hindgut). Prolonged culture of cells induced for 4 to 5 days to form endoderm by Activin A leads to an increase of CDX2 and a loss of SOX2, suggesting posteriorization in these conditions. Anteriorization of definitive endoderm may be accomplished by withdrawing or blocking Activin A and adding anteriorizing morphogens. Preferred anteriorizing morphogens are inhibitors of BMP and TGF-beta signaling. Tnhibitors of BMP and TGF-beta signaling may be used singly or in combination. Preferably, inhibitors of BMP and TGF-beta signaling are used in combination. Examples of BMP inhibitors are Noggin, Chordin, and follistatin. A preferred inhibitor of BMP is Noggin. Examples of inhibitors of TGF-beta signaling are Ly364947 (SD208), SM16, SB-505124, SB-431542, and anti-TGF-beta antibodies. A preferred inhibitor of TGF-beta signaling is SB-431542. In a preferred embodiment, a combination of Noggin and SB-431542 is used to induce anteriorization of definitive endoderm. In certain embodiments, a combination of Noggin and SB-431542 is added at day 4-5 of culture to induce anteriorization of definitive endoderm.

Anteriorization of definitive endoderm with Noggin and SB may be confirmed by, for example, detecting expression of, for example, one or more of SOX2, TBX1 (pharynx), PAX9 (pharynx, thymus), FOXP2 (lung, airway epithelium), DLX3 (esophagus), FOXA2 (definitive endoderm), and/or SOX7 (early endodermal marker); and optionally detecting lack of expression of PAX6 (ectoderm) and/or BRACHYURY (mesoderm).

Cell Populations

In certain embodiments, the invention thus provides cell populations enriched for anterior foregut endoderm cells. Enriched populations of anterior foregut endoderm comprise at least 25%, e.g., at least 50%, at least 75%, at least 90%, at least 95% at least 99% or at least 99.9% anterior foregut endoderm cells.

In certain embodiments, the invention provides cell populations enriched for pharyngeal endoderm cells. Enriched populations of pharyngeal endoderm comprise at least 25%, e.g., at least 50%, at least 75%, at least 90%, at least 95% at least 99% or at least 99.9% pharyngeal endoderm cells.

In certain embodiments, the invention provides a method of deriving anterior foregut endoderm comprising culturing definitive endoderm with an inhibitor of BMP or an inhibitor of TGF-beta signaling and in the absence of Activin A. In preferred embodiments, definitive endoderm is cultured with both an inhibitor of BMP and an inhibitor of TGF-beta signaling and in the absence of Activin A.

In some embodiments, an inhibitor of BMP is Noggin. In some embodiments of the methods described herein, Noggin is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, Noggin is present in cultures at a concentration of about 25 ng/ml to 150 ng/ml, 50 ng/ml to 150 ng/ml or 75 ng/ml to 150 ng/ml. In most preferred embodiments, Noggin is present in cultures at a concentration of about 100 ng/ml.

In some embodiments, an inhibitor of TGF-beta is SB-431542. In some embodiments of the methods described herein, SB-431542 is present in cultures at a concentration of about 0.1 µM to 1 mM, 1 µM to 100 µM, 1 µM to 500 µM, 1 µM to 250 µM, or 1 µM to 100 µM. In preferred embodiments, SB-431542 is present in cultures at a concentration of about 5 µM to 250 µM, 5 µM to 100 µM, 5 µM to 50 µM, or 5 µM to 25 µM. In most preferred embodiments, SB-431542 is present in cultures at a concentration of about 10 µM.

Also preferred are embodiments wherein cultures used in the methods of the invention comprise Noggin at a concentration of about 75 ng/ml to 150 ng/ml and SB-431542 at a concentration of about 5 µM to 25 µM.

Induction of Ventral Anterior Foregut Endoderm

Most organs derived from the most anterior foregut endoderm, such as thymus, parathyroid glands, trachea and lung are derived from the ventral or ventrolateral aspects of the anterior foregut endoderm.

Anterior foregut endoderm induced by Noggin/SB431542 may be further induced to form ventralized anterior foregut endoderm by treatment with one or more agonists of the Wnt signaling, FGF signaling, BMP signaling, and EGF signaling pathways. Effective induction of ventral anterior foregut endoderm is dependent upon treatment with Noggin/SB431542. Tissue induced to form ventral anterior foregut endoderm may be identified by, e.g., the markers NKX21 and NKX2.5.

In some embodiments, anterior foregut endoderm is ventralized (i.e., induced to form ventralized anterior foregut endoderm) by a combination of two or more agonists of the Wnt signaling, FGF signaling, BMP signaling, and EGF signaling pathways. Further preferred, are embodiments wherein anterior foregut endoderm is ventralized by a combination of two or more agonists of the Wnt signaling, FGF signaling, BMP signaling, and EGF signaling pathways, three or more agonists of the Wnt signaling, FGF signaling, BMP signaling, and EGF signaling pathways, four or more agonists of the Wnt signaling, FGF signaling, BMP signaling, and EGF signaling pathways, or five or more agonists of the Wnt signaling, FGF signaling, BMP signaling, and EGF signaling pathways.

In some embodiments, an agonist of Wnt signaling is Wnt3a, which mediates canonical Wnt signaling; any inducer of canonical Wnt signaling can be used, for example, Wnt/beta-catenin pathway agonists glycogen synthase kinase 3 beta (GSK3b) inhibitors, or casein kinase 1 (CK1) inhibitors. Non-limiting examples of Wnt agonists include DNA encoding β-catenin (e.g., naked DNA encoding β-catenin, plasmid expression vectors encoding β-catenin, viral expression vectors encoding β-catenin), β-catenin polypeptides, one or more Wnt/β-catenin pathway agonists (e.g., selected from the group consisting of Wnt ligands, DSH/DVL-1, -2, -3, LRP6N, WNT3A, WNT5A, and WNT3A, 5A), one or more glycogen synthase kinase 3 β (GSK3β) inhibitors (e.g., selected from the group consisting of lithium chloride (LiC1), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl) urea (AR-A014418), indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5-bromoindirubin, 4-Benzyl-2-methyl-1,2,4-thiadiazolidine-3,5-dione (TDZD-8), 2-thio(3-iodobenzyl)-5-(1-pyridyl)[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), H-KEAPPAPPQSpP-NH2 (L803) and Myr-N-GKEAPPAPPOSpP-NH2 (L803-mts)), one or more anti-sense RNA or siRNA that bind specifically to GSK3 (3 mRNA, one or more casein kinase 1 (CK1) inhibitors (e.g., antisense RNA or siRNA that binds specifically to CK1 mRNA), one or more protease inhibitors, one or more proteasome inhibitors. When WNT3a is used in the methods described herein, Wnt3a is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, Wnt3a is present in cultures at a concentration of about 25 ng/ml to 150 ng/ml, 50 ng/ml to 150 ng/ml or 75 ng/ml to 150 ng/ml. In further preferred embodiments, Wnt3a is present in cultures at a concentration of about 100 ng/ml.

In preferred embodiments, agonists of FGF signaling are used, e.g., FGF7, FGF9, or FGF10. For use in the methods described herein, FGF7 or FGF10 are present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, FGF7 or FGF10 are present in cultures at a concentration of about 25 ng/ml to 150 ng/ml, 50 ng/ml to 150 ng/ml or 75 ng/ml to 150 ng/ml. In most preferred embodiments, both FGF7 and FGF10 are present in cultures at a concentration of about 10 ng/ml. In some embodiments other agonists of FGF signaling can be used, e.g., FGF1, 2, 3, 5, 6, 9, 11, 12, 13, 14, 15, 16, 17, 18, 19, 20, 21, 22, or 23.

In preferred embodiments, an agonist of EGF signaling is EGF. For use in the methods described herein, EGF is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, EGF is present in cultures at a concentration of about 25 ng/ml to 150 ng/ml, 50 ng/ml to 150 ng/ml or 75 ng/ml to 150 ng/ml. In most preferred embodiments, both EGF is present in cultures at a concentration of about 20 ng/ml.

In preferred embodiments, an agonist of BMP signaling is BMP-4, though in some embodiments another BMP may be used, e.g., any of BMP-1 to -20, e.g., any of BMP 2-7. For use in the methods described herein, BMP-4 is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, BMP-4 is present in cultures at a concentration of about 25 ng/ml to 150 ng/ml, 50 ng/ml to 150 ng/ml or 75 ng/ml to 150 ng/ml. In most preferred embodiments, both BMP-4 is present in cultures at a concentration of about 10 ng/ml.

In a most highly preferred embodiment, FGF7, FGF10, EGF, BMP-4 and Wnt3a are present at concentrations of 10, 10, 20, 10 and 100 ng/ml, respectively.

Induction of Early Lung Markers from Ventralized Endoderm

Ventralized anterior foregut endoderm that expresses the lung marker GATA6 can be induced by treatment with retinoic acid (RA) in combination with one or more factors selected from the group consisting of Wnt ligands, Wnt signaling activators, BMPs, epidermal growth factors (EGFs) and fibroblast growth factors (FGFs). In some embodiments, the induction of lung markers (e.g., the generation of cells or tissues expressing lung markers) is promoted by culturing definitive endoderm in the presence of Wnt3a, FGF10, FGF7, BMP4, EGF, and RA.

In preferred embodiments, retinoic acid is all-trans transretinoic acid (ATRA). For use in the methods described herein, ATRA is present in cultures at a concentration of about 1 nM to 10 µM, 1 nM to 100 µM, 5 nM to 10 µM, 5 nM to 1 µM, 50 nM to 1 µM and 100 nM to 5 µM. In preferred embodiments, ATRA is present in cultures at a concentration of about 100 nM to 1 µM, or 1 µM to 5 µM. In most preferred embodiments, ATRA is present in cultures at a concentration of about 1 µM. In some embodiments, ATRA is used in combination with the factors described above to induce a ventral anterior foregut that is more biased towards the lung field as opposed to the pharyngeal region.

Induction of the Terminal Lung Marker SP-C

Continued treatment with Wnt3a, FGF10, FGF7, BMP4, EGF and RA until day 19 yielded low levels of the terminal alveolar type II cell marker SP-C. Optimal expression of SP-C was achieved when these factors were replaced at day 11 by Wnt3a, FGF7 and FGF10.

In preferred embodiments, the terminal lung marker SP-C is induced from anterior foregut endoderm ventralized in the presence of RA and a combination of two or more agonists of the Wnt signaling, FGF signaling, and a BMP.

In some embodiments, an agonist of Wnt signaling is Wnt3a; others can also be used, as described herein. For use in the methods described herein, Wnt3a is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, Wnt3a is present in cultures at a concentration of about 25 ng/ml to 150 ng/ml, 50 ng/ml to 150 ng/ml or 75 ng/ml to 150 ng/ml. In further preferred embodiments, Wnt3a is present in cultures at a concentration of about 100 ng/ml.

In some embodiments, agonists of FGF signaling are FGF7 or FGF10; others can also be used, as described herein. For use in the methods described herein, FGF7 or FGF10 are present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, FGF7 or FGF10 are present in cultures at a concentration of about 25 ng/ml to 150 ng/ml, 50 ng/ml to 150 ng/ml or 75 ng/ml to 150 ng/ml. In most preferred embodiments, both FGF7 and FGF10 are present in cultures at a concentration of about 10 ng/ml.

In a most highly preferred embodiment, FGF7, FGF10, and Wnt3a are present at concentrations of 10, 10, and 100 ng/ml, respectively.

Induction of the Specific Parathyroid Marker GCMB

Induction of the specific parathyroid marker from ventralized anterior foregut endoderm was achieved when anterior foregut endoderm was ventralized in the presence of Wnt3a, FGF10, FGF7, BMP4, EGF, followed by removal of these factors at day 11 and addition of either SHH, FGF8, or both.

In preferred embodiments, the specific parathyroid marker SP-C is induced from ventralized anterior foregut endoderm by a combination of one or more agonists of the SHH and FGF8 signaling, In preferred embodiments, an agonist of SHH signaling is SHH. For use in the methods described herein, SHH is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, SHH is present in cultures at a concentration of about 25 ng/ml to 150 ng/ml, 50 ng/ml to 150 ng/ml or 75 ng/ml to 150 ng/ml. In further preferred embodiments, Wnt3a is present in cultures at a concentration of about 100 ng/ml.

In preferred embodiments, an agonist of FGF signaling is FGF8. For use in the methods described herein, FGF8 is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, FGF8 is present in cultures at a concentration of about 25 ng/ml to 150 ng/ml, 50 ng/ml to 150 ng/ml or 75 ng/ml to 150 ng/ml. In most preferred embodiments, both FGF8 is present in cultures at a concentration of about 10 ng/ml.

In a most highly preferred embodiment, FGF8 and SHH are present at concentrations of 10 and 100 ng/ml, respectively.

Methods of Screening

In certain embodiments, the invention provides methods for identifying an agent that affects the proliferation, differentiation or survival of anterior foregut endoderm cells. The methods comprise culturing an enriched population of anterior foregut endoderm cells in the presence of an agent to be tested and comparing the proliferation, differentiation or survival of said cells in the presence and absence of said agent, wherein a difference in the presence of said agent is indicative of the identification of an agent that affects the proliferation, differentiation or survival of said cells.

In certain embodiments, the invention provides methods for identifying a gene involved in cell differentiation. The methods comprise isolating definitive endoderm cells and anterior foregut endoderm cells and comparing the gene expression profiles of said definitive endoderm cells and said anterior foregut endoderm cells, wherein identification of a gene that is differentially expressed between said definitive endoderm cells and said anterior foregut endoderm cells is indicative of a gene involved in cell differentiation. Methods of determining gene profiles are well known in the art.

In certain embodiments, the invention provides a method of identifying an antibody that recognizes a molecular marker of progression from definitive endoderm to anterior foregut endoderm comprising raising antibodies to and enriched population of anterior foregut endoderm cells and screening for an antibody that binds to said anterior foregut endoderm significantly higher than said antibody binds to said definitive endoderm. Methods of raising and screening antibodies are well known in the art. A preferred antibody is a monoclonal antibody.

Cell Replacement Therapies

Anterior foregut endoderm cells derived by a method described herein from pluripotent cells are useful in generating cells or tissues for cell replacement therapy to treat conditions arising from damage to or absence of tissue derived therefrom, such as, for example and without limitation, conditions were the thyroid is not functional (hypothyroidism) because of genetic mutations, autoimmune attack or surgical removal (for hyperthyroidism or thyroid cancer); hypoparathyroidism, either from genetic causes, or arising after surgical ablation; lung injury; thymus epithelium, e.g., damaged by allogeneic hematopoietic stem cell transplantation (HSCT) or absent because of congenital disease (Digeorge syndrome and Nude/SCID syndrome).

Figure 1B:
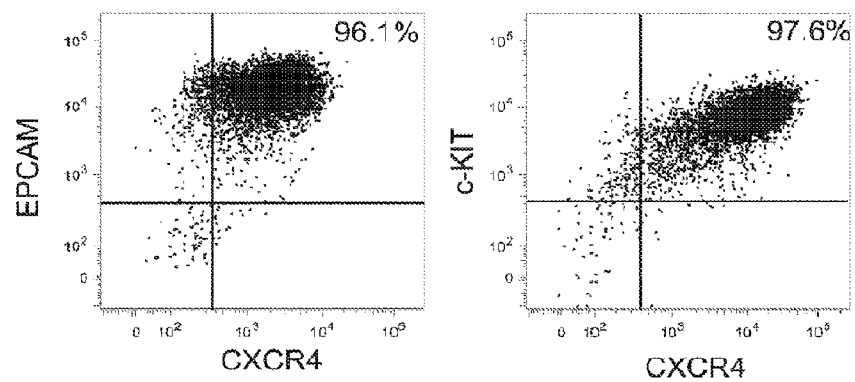
Figures 1, 1C:
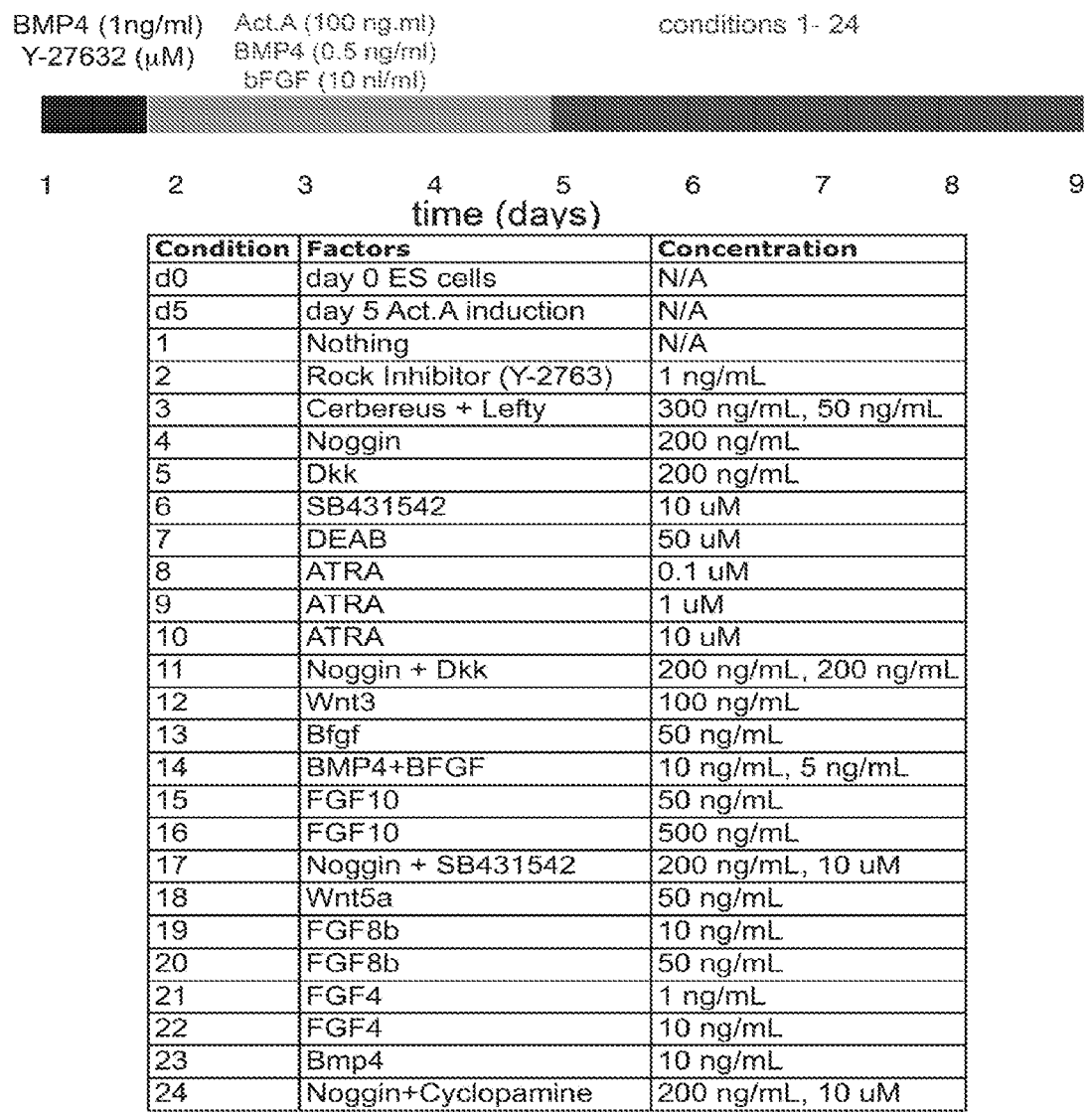
Figures 1, 1C, 2:
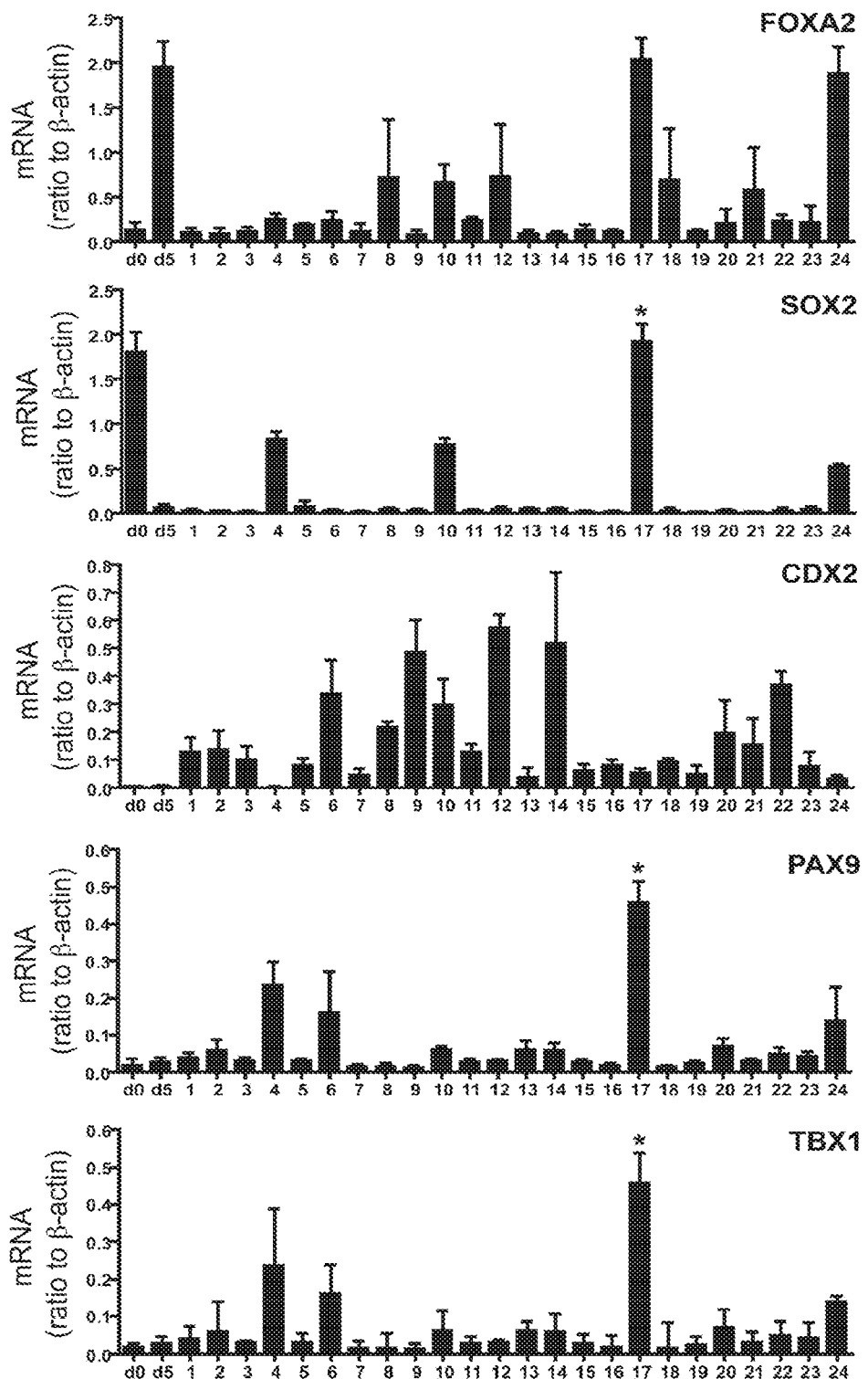
Figure 1D:
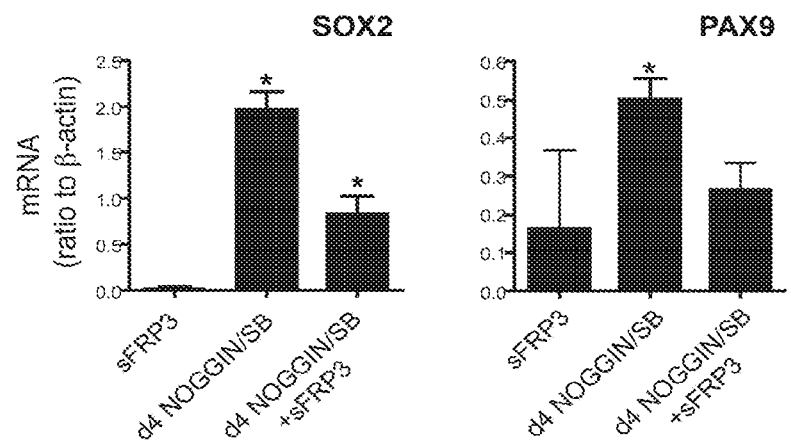
Figure 1E:
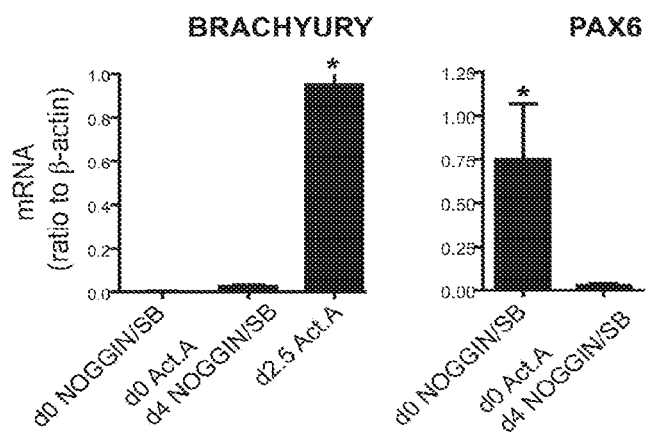

In some embodiments, cells, e.g., thymic epithelial cells (TECs) derived from ES or iPS cells by a method described herein could also improve humanized mouse models (FIG. 1e). A major challenge in immunology is establishing mouse models of the human immune system. Currently the best models are immunodeficient Rag1$^{-/-}$ilr2g$^{-/-}$ or NOD$^-$SCIDilr2g$^{-/-}$ mice engrafted neonatally with human cord blood hematopoietic stem and progenitor cells. In such mice, all major hematopoietic lineages are reconstituted and even the structure of secondary lymphoid organs appears 'human'. However, human T cell responses are weak except for alloreactivity, and peripheral T cell homeostasis abnormal (Manz, Immunity. 26:537-541 (2007); Traggiai et al., Science. 304:104-107 (2004); Legrand et al., Methods Mol Biol. 415:65-82 (2008); Gimeno et al., Blood. 104:3886-3893 (2004)). An improvement of this model with more robust T cell activity is the BLT mouse (Lan et al., Blood. 2006; 108:487-492; Melkus et al., Nat Med. 12:1316-1322 (2006)). This is a NOD-SCIDilr2g$^{-/-}$ mouse transplanted with a human fetal thymus and liver under the kidney capsule and subsequently transplanted with fetal liver CD34+ progenitor cells. In these mice innate as well as MHC I and II-restricted, T cell-dependent immune responses were observed. Interestingly, all T cell development occurred in the grafted human thymus, and not in the endogenous mouse thymus. These data suggest that the presence of human thymic tissue may be critical to develop a humanized mouse. It follows that as TECs are the essential functional component of the thymus, ES or iPS-derived TECs could also be used to construct an improved humanized mice. In addition, by using patient-specific iPS cells it is possible to the capture some of the genetic diversity in disease susceptibility and immune responses among humans in a mouse model. Finally, iPS technology will allow co-transplantion of syngeneic human tissues. In such a mouse, organ or tissue-specific immune responses in the context of autoimmunity or infection can be studied, or vaccines can be tested. As one example, a mouse model of an autoimmune or immune-mediated disease can be created by transplanting into immune deficient mice bone marrow stem cells and TECs derived as described herein (e.g., from skin-cell derived iPS cells), both from a human subject with the autoimmune or immune-mediated disease (e.g., rheumatoid arthritis, diabetes, multiple sclerosis, psoriasis, or colitis). In some embodiments, both the bone marrow stem cells and the TECs are from the same subject, and in some embodiments they can be from different subjects. The bone marrow blood stem cells will go to the human-derived thymus and make T cells there. This can be used to model autoimmune disease (and any other immune-mediated disease) in mice. In some embodiments, the methods further include transplanting iPS derived human autoimmune target tissues (e.g., islets in the case of diabetes).

EXAMPLES

The invention is further described in the following examples, which do not limit the scope of the invention described in the claims.

Example 1. Generation of Anterior Foregut Endoderm from Human Embryonic and Induced Pluripotent Stem Cells The following Materials and Methods were used in this Example.

Cells and Culture Conditions.

hESC (HES2, National Institutes of Health code ES02 from ES Cell International; passages 25-33) were cultured on mouse embryonic fibroblasts plated at 8,000-12,000 cells/cm², A medium of DMEM/F12, 20% knockout serum replacement (Gibco), 0.1 mM β-mercaptoethanol (Sigma-Aldrich), and 20 ng/ml FGF-2 (R&D) was changed daily. Cells were passaged with trypsin, washed and replated at a dilution of 1:5 to 1:10. HDF2 and HDF9, hiPS cell lines, were cultured as hES2. hES and hiPS cultures were maintained in a 5% $CO_2$/air environment, and hES differentiations were maintained in a 5% CO2/5% O2/90% $N_2$ environment.

Endoderm Induction.

Mouse embryonic fibroblasts were depleted by a 24 h passage on Ma gel (Gibco) with Y-27632 (10 μM), and embryoid bodies were formed on low-adherence dishes (Costar). During embryoid body formation and differentiation, HES2 cells were reseeded at the same concentration (1:1 dilution), whereas HDF2 and HDF9 required a higher seeding (2:1-4:1 concentration) for efficient endoderm generation. Differentiations were performed in a medium of DMEM/F12 (Invitrogen) supplemented with N2 (Gibco), B27 (Gibco), ascorbic acid (50 μg/ml, Sigma). Glutamax (2 mM, Invitrogen), monothioglycerol (0.4 μM, Sigma). The following concentrations of factors were used for primitive streak formation, endoderm induction, anterior/pharyngeal endoderm induction, and subsequent anterior posterior and dorsoventral patterning: human BMP-4, 1 ng/ml and 10 ng/ml; human bFGF, 2.5 ng/ml; human activin A, 100 ng/ml; human Noggin, 200 ng/ml; Y-27632, 1 μM; SB-431542, 10 μM; human FGF10, 10 ng/ml; human FGF7, 10 ng/ml; murine EGF 20 ng/ml; and human WNT3a, 100 ng/ml. Hepatic conditions were as previously described 2 and contain BMP-4, 50 ng/ml; bFGF, 10 ng/ml; VEGF, 10 ng/ml; HGF, 10 ng/ml; TGFα, 20 ng/ml; dexamethasone, 40 ng/ml. All factors were purchased from R&D systems, except SB-431542 and Y-27632, which are from Tocris, and dexamethasone (Sigma). The factors were added in the following sequence: day 1, Y-27632; days 1-5, BMP4, bFGF and activin A; days 5-9, Noggin and SB-431542; days 7-19 WNT3a, FGF10, BMP4, FGF7 and EGF. For hepatic differentiation, factors were added in the following sequence: day 1. Y-27632; days 1-5, BMP4, bFGF and activin A; days 5-9, dexamethasone, bFGF, HGF, VEGF, EGF, TGFa and BMP4. For some experiments, 500 μM all-trans retinoic acid (Sigma) was added to the cultures. At day 5, embryoid bodies were trypsinized (Gibco) and plated at 10,000-50,000 cells/cm2 in gelatin-coated, tissue culture-treated dishes (Fisher).

The day 11 screen of morphogens (FIG. 2h) included pairwise and some higher order of magnitude additions of FGFS (FGF10+FGF7) (R&D Systems), SU-5402 (EMD Chemicals), Wnt5a (R&D Systems), WNT3a (R&D Systems), sFRP1 (R&D Systems), BMP4, Noggin, SHH (R&D Systems), cyclopaminc (EMD Chemicals), SB-431542, TGF-β1 (R&D Systems), DAPT (EMD Chemicals), retinoic acid (Sigma), DEAB (Sigma), EGF (R&D Systems), tyrophastin AG-1478 (EMD Chemicals) and WP1066 (EMD Chemicals).

Quantitative PCR.

Total RNA was extracted using Trizol (Invitrogen), phase lock tubes (5′ Prime) and the RNeasy kit (Qiagen). 1-2 μg of total RNA were treated with DNase 1 (Qiagen) and reverse transcribed it using random hexamers and Superscript III (Invitrogen). Amplified material was detected using Sybr-Green (Invitrogen). Real-time quantitative PCR was performed on ABI 7900HT thermocycler (Applied Biosystems), with a 10-min step at 95° C. followed by 40 cycles of 95° C. for 15 s and 60° C. for 1 min. All experiments were done in triplicate with SYBR GreenER quantitative PCR SuperMix (Invitrogen). Denaturing curves for each gene were used to confirm homogeneity of the DNA product. Absolute quantification was obtained in relation to a standard curve of genomic DNA dilution series. Quantified values for the gene of interest were normalized against input determined by the housekeeping genes GAPDH and β-ACTIN, qPCR for each culture well was performed in triplicate. Primer sequences are listed in Table 1.

TABLE 1

Gene Forward Primers (5′ to 3′) and Reverse Primers (5′ to 3′)

| Gene | Forward | SEQ ID NO | Reverse | SEQ ID NO |
|---|---|---|---|---|
| SOX2 | GCACATGAAGG AGCACCCGGAT TA | 1 | CGGGCAGCGTG TACTTATCCTT CTT | 2 |
| GCM2 | CAGAGTGGGTC CCTTCTTTACC TACAAC | 3 | TGCCTTTCACA TTTCCCTGCCT | 4 |
| PAX1 | TTAGACTGCCG TACCCTCCTCA CAA | 5 | AGGAAGGGAAA GAGAAAGGGAA GGGA | 6 |
| SFTPC | CCTTCTTATCG TGGTGGTGGTG GT | 7 | TCTCCGTGTGT TTCTGGCTCAT GT | 8 |
| ACTB | TAAGTCCTGCC CTCATTTCCCT CT | 9 | TTTGCGGATGT CCACGTCACAC TT | 10 |
| GATA6 | AGTTCCTACGC TTCGCATCCCT TC | 11 | TGAACAGCAGC AAGTCCTCCCA | 12 |
| TBX1 | CGGCTCCTACG ACTATTGCCC | 13 | GGAACGTATTC CTTGCTTGCCC T | 14 |
| SOX17 | CTGTTGAATCA TAAGCTTGACC TGCCC | 15 | ATCTTAAACCC AGCGATGCTTG CC | 16 |
| PAX6 | GGGATGAGGAT GCATTGTGGTT GT | 17 | GAGGAAGAAGA GGGAGAAGAAG GAAGAGG | 18 |

TABLE 1-continued

Gene Forward Primers (5' to 3')
and Reverse Primers (5' to 3')

| Gene | Forward | SEQ ID NO | Reverse | SEQ ID NO |
|---|---|---|---|---|
| PAX9 | TGGTTATGTTG CTGGACATGGG TG | 19 | GGAAGCCGTGA CAGAATGACTA CCT | 20 |
| CDX2 | TAAATGCCAGA GCCAACCTGAC TTCC | 21 | CAGCAGCAACA ACAACACAAAC TCCC | 22 |
| FOXP2 | TCAGCAAATGC AGCAGATCCTT CAG | 23 | ACAGCCTGCTG TTGTTGGAGAA G | 24 |
| MIXL1 | CTGTGCTCCTG GAACTGAAACG AA | 25 | TGACCTTGGGA GCTAGAGTCAG AGATG | 26 |
| BRACH-YURY | CAGTGGCAGTC TCAGGTTAAGA AGGA | 27 | CGCTACTGCAG GTGTGAGCAA | 28 |
| NXK2.5 | TGGAGAAGACA GAGGCGGACAA | 29 | ATAGACCTGCG CCTGCGAGAA | 30 |
| NKX2.1 | CGGCATGAACA TGAGCGGCAT | 31 | GCCGACAGGTA CTTCTGTTGCT TG | 32 |
| ODD1 | CAGCTCACCAA CTACTCCTTCC TTCA | 33 | TGCAACGCGCT GAAACCATACA | 34 |
| CREB313 | TCTCCAGAACT TTGCACAACGA TGC | 35 | TCCTCCGTCGA ATTGGTCAGGT T | 36 |
| CEBPA | AGAAGTCGGTG GACAAGAACAG CA | 37 | ATTGTCACTGG TCAGCTCCAGC A | 38 |

Flow Cytometry.

Day 5 embryoid bodies or day 13 monolayer cultures were dissociated with trypsin/EDTA (2 min). The cells were stained with directly conjugated CXCR4 (Invitrogen), c-KIT (BD Biosciences) and EPCAM (BD Biosciences) in IMDM complemented with 10% serum. Cells were analyzed on a LSRII. Flowjo software (Tree Star) was used for all analyses.

Immunofluorescence.

Day-7, -9 or -13 cultures were fixed with fresh paraformaldehyde (4%) for 30 min at 25° C. and then washed in PBS. The cells were permeabilized and blocked in a solution with 0.1% saponin, 0.1% BSA, 10% FCS (Gemstar) and 10% fetal donkey serum (Jackson Immunofluorescence). For three-dimensional cultures, cells were embedded at day 5 in Matrigel using the "embedded" and "on-top" assays, as previously described (Lee e al., Nat. Methods 4, 359-365 (2007)). Cultures were embedded in Optimal Cutting Temperature (OCT, Tissue Tek) at day 9, extracted, sectioned and processed as above. Primary antibodies were added overnight, and include PAX-9 (Abcam), TBX1 (Abcam), SOX2 (Stemgent, Santa Cruz), CDX2 (Abcam), NKX2-1 (Invitrogen) and AIRE (Santa Cruz). Cells were washed and incubated with donkey anti-mouse whole IgG-Dylight488, donkey anti-goat whole IgG-Cy3, and donkey anti-rabbit whole IgG-Cy5 for 1 hour (h). The cells were washed, and nuclei were stained with DAPI (Invitrogen). Stains were visualized using a fluorescence microscope (Leica DMI 4000B, Wetzlar, Germany). This instrument was fitted with a DFC340 Fx Monochrome Cooled Digital Camera for fluorescent acquisition (Leica) and variable objective lenses (5×-40×) were used. Filter models: A4 UV, 11504135; GFP, 11532366; YFP 1153267; RFP, 11513894; CY3, 11600231. Exposure settings varied, but were set based on hepatic-specified cultures differentiated and stained in parallel. Images were acquired using Leica Application Suite Advanced Fluorescence Software Package AF6000 (Leica) in PBS at 25° C. Images are shown without rendering or deconvolution. Images were digitally processed using Adobe Photoshop CS4 (Adobe) by altering only contrast and brightness, and these manipulations were performed on hepatic specified and experimental conditions simultaneously. Quantification was performed by counting a minimum of ten random fields at 20× magnification. On most panels, the magnification by the lens objective is listed.

Mice.

NOD.Cg-PrkdcscidI12rgtm1Wjl/SzJ (NOD/SCIDII2rg−/−) mice were purchased from Jackson Laboratory. Animals were kept in a specific pathogen-free facility. Experiments and animal care were performed in accordance with the Mount Sinai Institutional Animal Care and Use Committee. One million cells were injected under the kidney capsule. Outgrowths were excised, embedded in OCT and analyzed using hematoxylin and eosin stains for morphology or immunofluorescence for specific antigens as above.

Statistical Analysis.

For statistical analysis, unpaired t-test and when more than two groups were compared, one-way ANOVA was used. Results are expressed as mean±s.e.m.

Results

Definitive endoderm, one of the three germ layers of the embryo proper, is induced from ES cells by high concentrations of activin A, mimicking nodal signaling during gastrulation 6. Examination of this process in the hES cell line HES2 by quantitative PCR revealed a transcriptional cascade in which the primitive streak marker MLYL1 and then the endodermal transcription factors SOX17 and FOXA2 are upregulated (FIG. 1a)(D'Amour et al., Nat. Biotechnol. 24, 1392-1401 (2006); Gouon-Evans et al., Nat. Biotechnol. 24, 1402-1411 (2006); Gadue et al., Proc. Natl. Acad. Sci. USA 103, 16806-16811 (2006); Zorn & Wells, Annu. Rev. Cell Dev. Biol. 25, 221-251 (2009); Yasunaga et al., Nat. Biotechnol. 23, 1542-1550 (2005)). After 4 d of exposure to activin A, >95% of the cells expressed the definitive endoderm markers CXCR4, c-KIT and EPCAM (FIG. 1b)(Yasunaga et al., Nat. Biotechnol. 23, 1542-1550 (2005)). After gastrulation, the definitive endoderm forms a tube with distinct anteroposterior axis identity (Zorn & Wells, Annu. Rev. Cell Dev. Biol. 25, 221-251 (2009)). Within definitive endoderm, the pluripotency marker SOX2 reemerges as a foregut marker, whereas CDX2 identifies hindgut (Sherwood et al., Dev. Dyn. 238, 29-42 (2009)). After activin A removal at day 5 of culture, an increase in both CDX2 and SOX2 expression was observed (FIG. 1a), suggesting the generation of a mixture of anterior and posterior definitive endoderm. Therefore, it was examined which signals added after induction of definitive endoderm favored anterior (SOX2+) and suppressed posterior (CDX2+) endoderm generation.

Figure 1F:
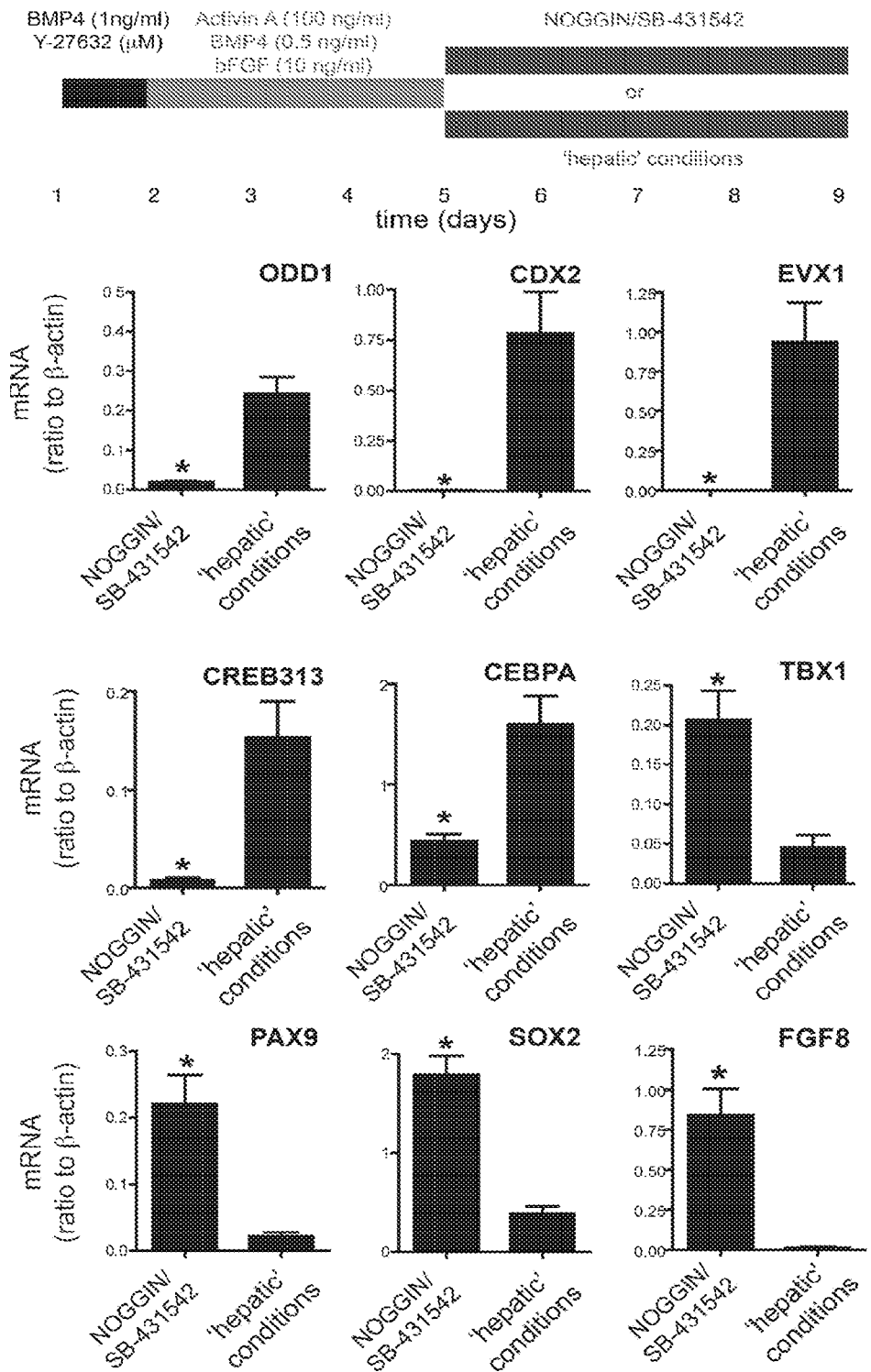
Figure 1G:
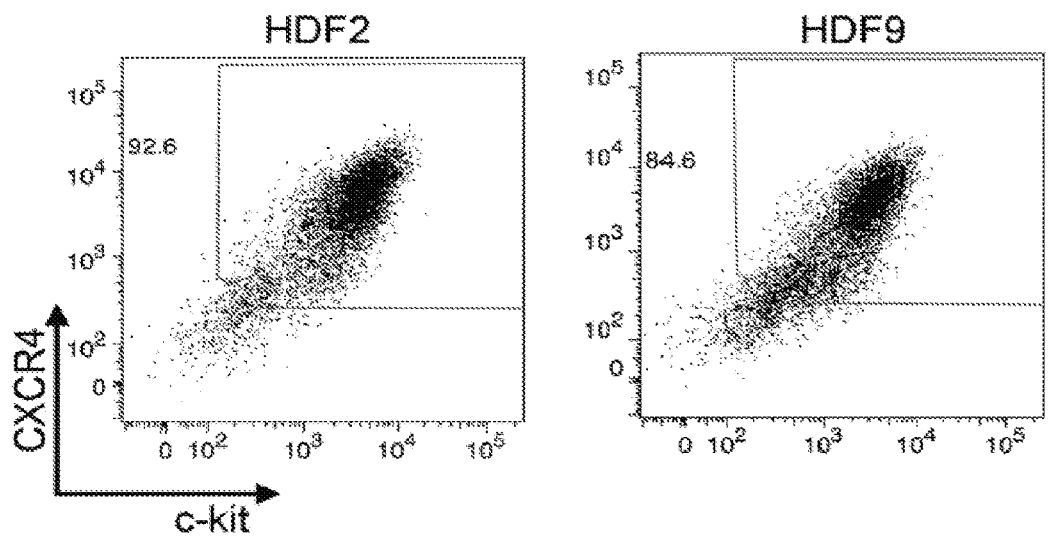
Figure 1H:
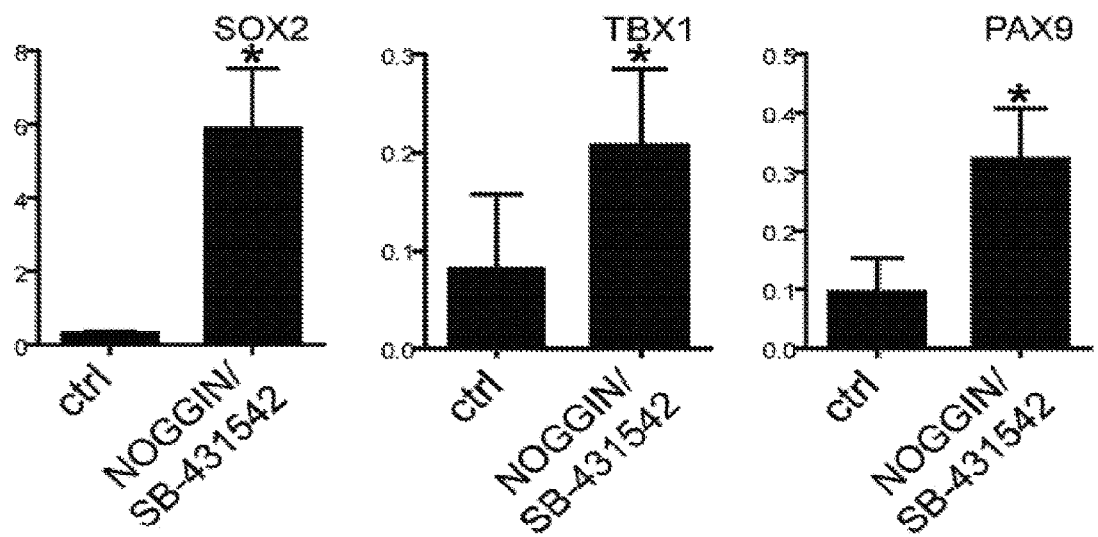
Figure 1I:
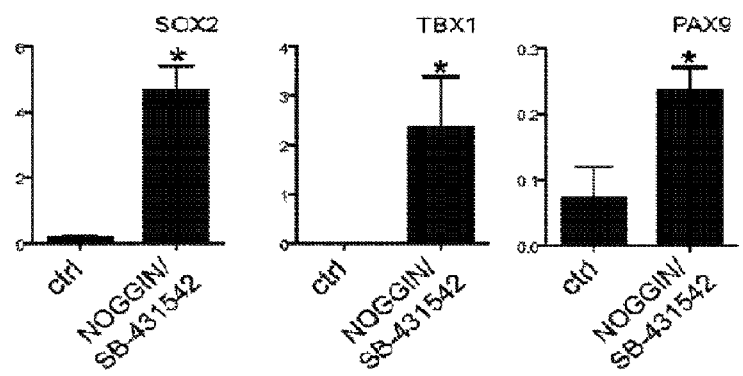

Following the generation of a CXCR4+EPCAM+ population in embryoid bodies exposed to activin A, the embryoid bodies were dissociated and plated as a monolayer. The addition of 24 combinations of morphogens and inhibitors at day 5 was tested (FIG. 1c), and expression of FOXA2, SOX2, CDX2. TBX1 (endoderm anterior to the stomach)(Graham, J. Exp. Zoolog. B Mol. Dev. Evol. 310, 336-344 (2008); Sherwood et al., Dev. Dyn. 238, 29-42 (2009); Peters et al., Genes Dev. 12, 2735-2747 (1998)) and PAX9 (pharyngeal endoderm)(Rodewald, Annu. Rev. Immunol. 26, 355-388 (2008); Peters et al., Genes Dev. 12, 2735-2747 (1998)) was used as readouts of cellular identity at day 9 of culture. Only in the combined presence of NOGGIN, a physiological inhibitor of BMP signaling, and SB-431542, a pharmacological inhibitor of activin A/nodal and TGF-β signaling, was SOX2 expression induced, CDX2 expression suppressed and FOXA2 expression maintained. Furthermore, only this condition induced strong expression of TBX1 and PAX9 (FIG. 1c). During the activin A-induction stage, cell number increased 4.5-±1.9-fold, and during the NOGGIN/SB-431542 stage, the cells expanded another 1.4-=0.4-fold. Notably, NOGGIN/SB-431542 treatment was equally potent in two hiPS cell lines (HDF2 and HDF9), with induction of SOX2, PAX9 and TBX1 (FIGS. 1g-i). Multiple FGF family members and WNT3a, consistent with their functions in development (Spence et al., Nature 470, 105-109 (2010); Gadue et al., Proc. Natl. Acad. Sci. USA 103, 16806-16811 (2006); Li et al., Genes Dev. 22, 3050-3063 (2008)), posteriorized definitive endoderm, as shown by increased CDX2 expression (FIG. 1c). However, WNT antagonism through addition of soluble Frizzled-related protein 3 (sFRP3) was not sufficient to induce SOX2 (FIG. 1c). Furthermore, sFRP3 did not synergize with NOGGIN/SB-431542, and even appeared detrimental for the induction of PAX9 and SOX2 (FIG. 1d). The timing of the addition of NOGGIN/SB-431542 was critical, as only treatment immediately after the generation of a uniform CXCR4+c-KIT+ or CXCR4+EPCAM+ population at day 5/6 induced a SOX2+ FOXA2 f population at day 9. Earlier administration abrogated gastrulation, and later administration failed to downregulate the posterior marker CDX2.

FOXA2 is also expressed in the notochord (mesoderm), and FOXA2 and SOX2 are co-expressed by the hindbrain floorplate (neurectoderm) (Wood & Episkopou, Mech. Dev. 86, 197-201 (1999); Weinstein et al., Cell 78, 575-588 (1994)). Furthermore, direct application of NOGGIN/SB-431542 to hES cells without prior endoderm induction by activin A leads to a neuroectodermal fate (Chambers et al., Nat. Biotechnol. 27, 275-280 (2009)). Therefore, the presence of these alternative fates was assayed. As expected, the neuroectodermal marker PAX6 was expressed in cultures where NOGGIN/SB-431542 was added at day 1, whereas BRACHYURY, a marker of the notochord and of gastrulating cells, was expressed during early endoderm induction (FIG. 1e). Neither BRACHYURY nor PAX6 were expressed in definitive endoderm exposed to NOGGIN/SB-431542 (FIG. 1e), indicating that NOGGIN/SB-431542 treatment of activin A-induced definitive endoderm specifies only AFE.

To further assess whether the NOGGIN/SB-431542-induced endodermal cells were distinct from previously described endodermal lineages, day 9 NOGGIN/SB-431542-treated cultures were compared with day 9 cultures grown under conditions favoring a hepatic (posterior foregut) fate. The latter has been previously shown to require BMP-4 and bFGF after activin A induction of endoderm (Gouon-Evans et al., Nat. Biotechnol. 24, 1402-1411 (2006)). The expression of CDX2, the hindgut marker EVX1, the liver markers CREB313 and CEBPA, as well as ODD1, a stomach domain marker (Sherwood et al., Dev. Dyn. 238, 29-42 (2009)), was higher in the 'hepatic' conditions than in the NOGGIN/SB-431542 conditions, and the reverse was true for the anterior markers TBX1, PAX9, SOX2 and FGF8, a marker within the endoderm specific for pharyngeal pouch endoderm (Vitelli et al., Development 129, 4605-4611 (2002)) (FIG. 1f). Therefore, NOGGIN/SB-431542 treatment specifies AFE cells that are distinct from those specified in hepatic conditions.

Application of NOGGIN/SB-431542 to activin A-induced definitive endoderm yielded colonies of densely packed cells surrounding an empty lumen-like or cyst-like opening. More than 90% of the cells were found in such colonies if plated at high density. Virtually all cells co-expressed SOX2 and FOXA2, although rare cells expressed only FOXA2. All colonies stained positive for TBX1, PAX9 and the pharyngeal endoderm marker FOXG1. The typical colonies observed in NOGGIN/SB-431542-treated cultures were never seen when cells were cultured in media without added factors. In these conditions, >95% of cells expressed FOXA2, but only rarely were SOX2+FOXA2+ cells observed. Colonies with this morphology were also never observed in hepatic conditions. Comparative immunofluorescence analysis of HES2-derived endodermal cells cultured in parallel in either NOGGIN/SB-431542 or hepatic conditions revealed that only NOGGIN/SB-431542 cultures were characterized by strong SOX2, PAX9 and TBX1, expression.

Collectively, these expression data show that NOGGIN/SB-431542 specifies a highly enriched population of cells with AFE phenotype in activin A-induced definitive endoderm. These findings are consistent with the fact that mice null for the BMP antagonist Chordin display anterior truncations (Bachiller et al., Development 130, 3567-3578 (2003)) and with the observation that activin A-induced endoderm contains a large fraction of CDX2+ posterior endoderm (FIG. 1a).

To determine the potential in vivo of cells cultured in NOGGIN/SB-431542 conditions, $10^6$ cells were transplanted under the kidney capsule of NOD/SCIDI12rg−/− mice. Whereas undifferentiated HES2 cells generated teratomas containing cells derived from all three germ layers, NOGGIN/SB-431542-treated cells produced growths lacking identifiable ectodermal or mesodermal elements. Multiple luminal structures were observed, lined either by pseudostratifed epithelium (typical of upper airway epithelium) or a more disorganized epithelium containing one to three layers of nuclei. The latter consistently stained for surfactant protein-C(SFTPC), a marker specific for type I alveolar cells in the lung. In hES cell-derived teratomas, no SFTPC staining was observed. The remainder of the cells stained almost uniformly for FOXA2. However, except in the luminal structures, FOXA2 was confined to the cytoplasm, possibly owing to differentiation into FOXA2-terminal AFE derivatives or to abnormal FOXA2 regulation in a xenograft. Islands of cells expressing PAX9, as well as rare regions showing discrete nuclear speckles of AIRE (specific for medullary thymic epithelial cells (Rodewald, Annu. Rev. Immunol. 26, 355-388 (2008))), were also detected. In hES-derived teratomas, PAX9 was only observed in zones of cartilage formation and AIRE expression was not observed. Collectively, these data suggest that the developmental potential of NOGGIN/SB-431542-induced definitive endoderm is largely limited to AFE derivatives in these conditions.

Next, these cells were further differentiated. AFE undergoes dorsoventral patterning, resulting in specification of lung buds, WNT, BMP and FGF signals from the ventral mesoderm (Rodewald, Annu. Rev. Immunol. 26, 355-388

Figure 2A:
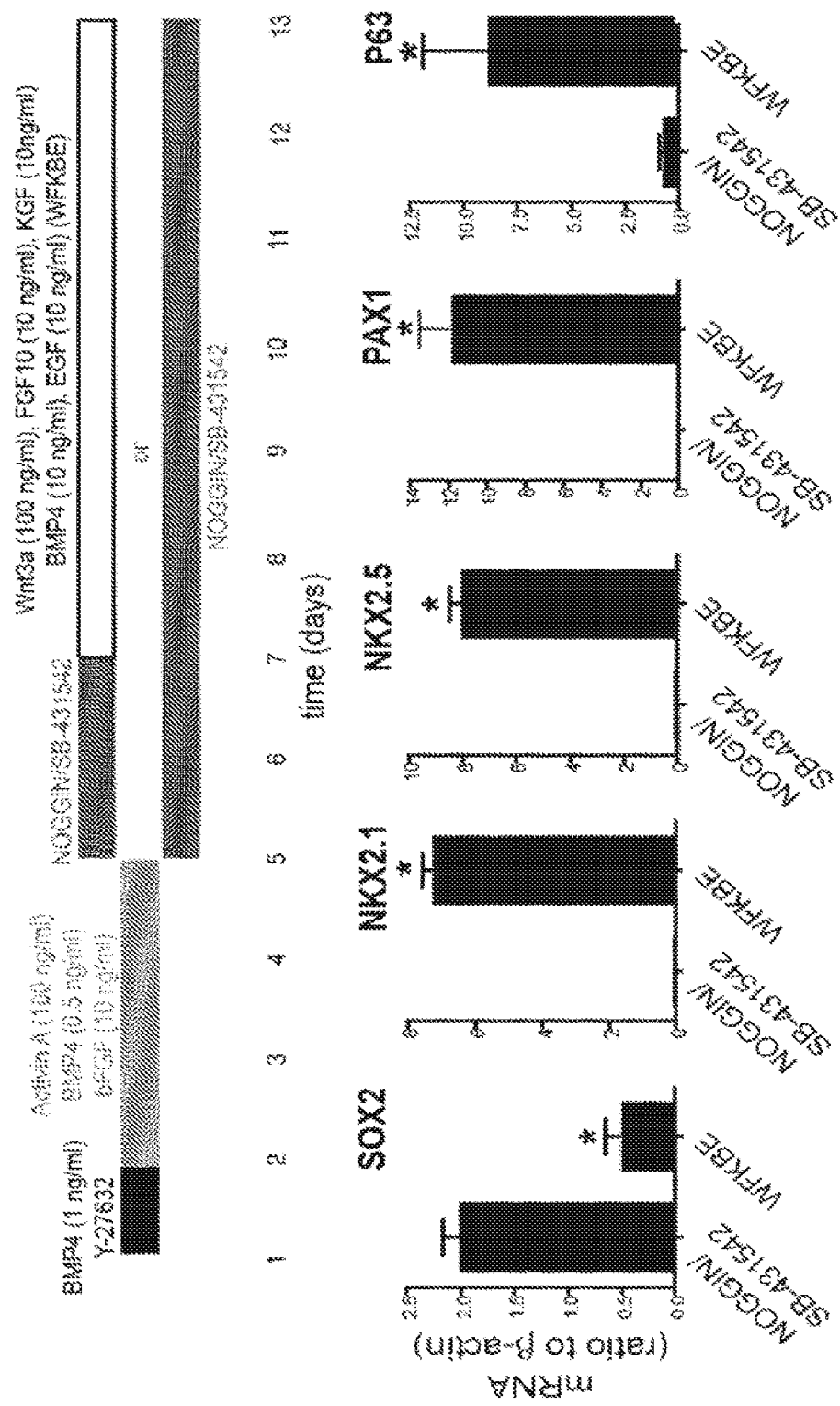
FIGS. 2a-c show the functional characteristics of NOGGIN/SB-431542-induced AFE cells. (2a) Expression of SOX2, NKX2.1, NKX2.5, PAX1 and P63 in HES2-derived cells generated in the two conditions schematically represented on top of the panel (n=6 culture wells from two independent experiments; *, significantly different from NOGGIN/SB-431542; P<0.05) WKFBE: WNT3a, KGF, FGF10, BMP4 and EGF. (2b) Expression of NKX2.1, NKX2.5 and PAX1 in HES2-derived cells generated in the three conditions schematically represented on top of the panel (n=4 to 6 culture wells from three independent experiments, *, significantly different from the other conditions; P<0.05). (2c) Schematic overview of the efficiency of induction of ventral AFE. WKFBE: WNT3a, KGF, FGF10, BMP4 and EGF.
Figure 2B:
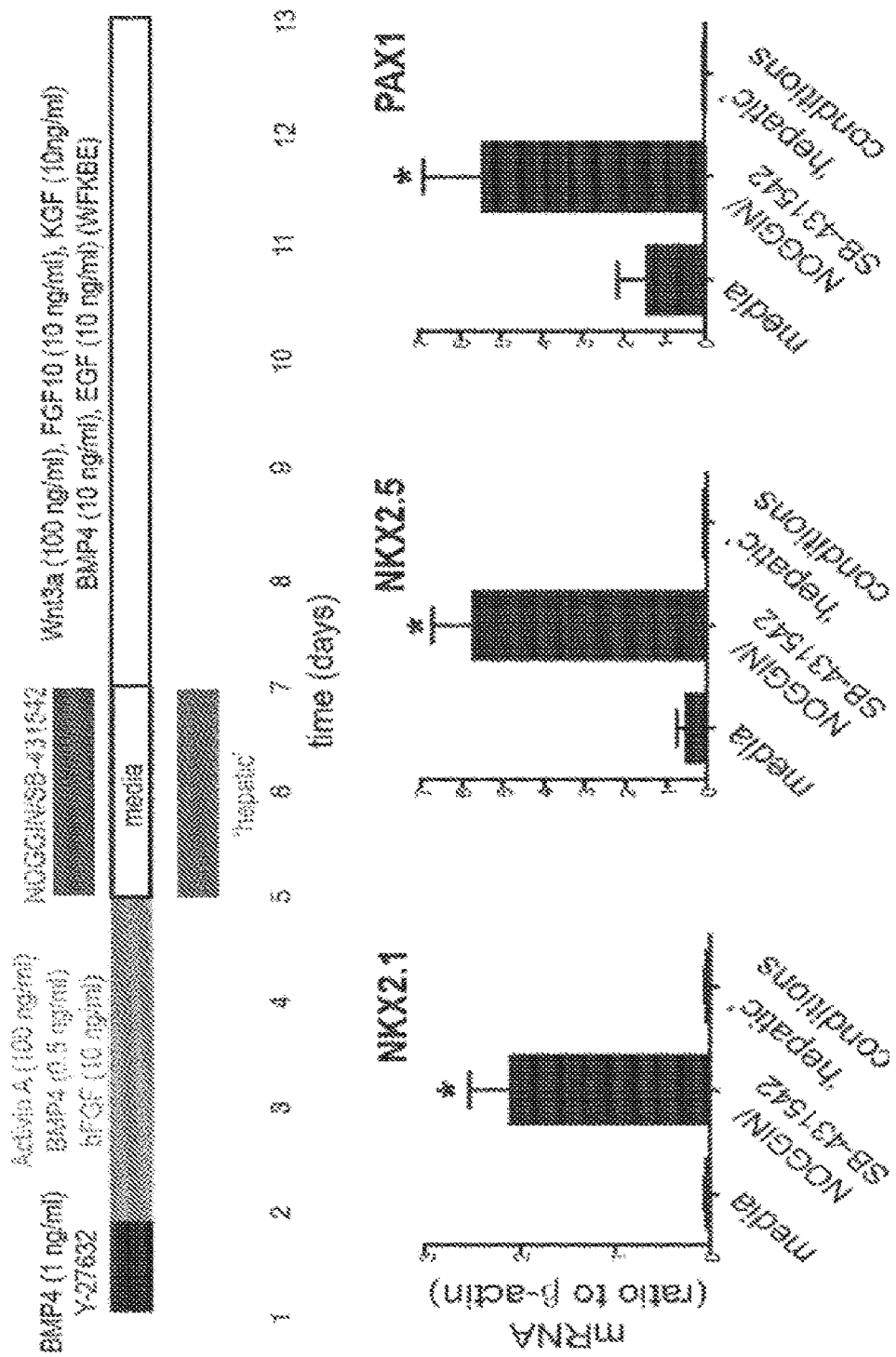
Figure 2C:
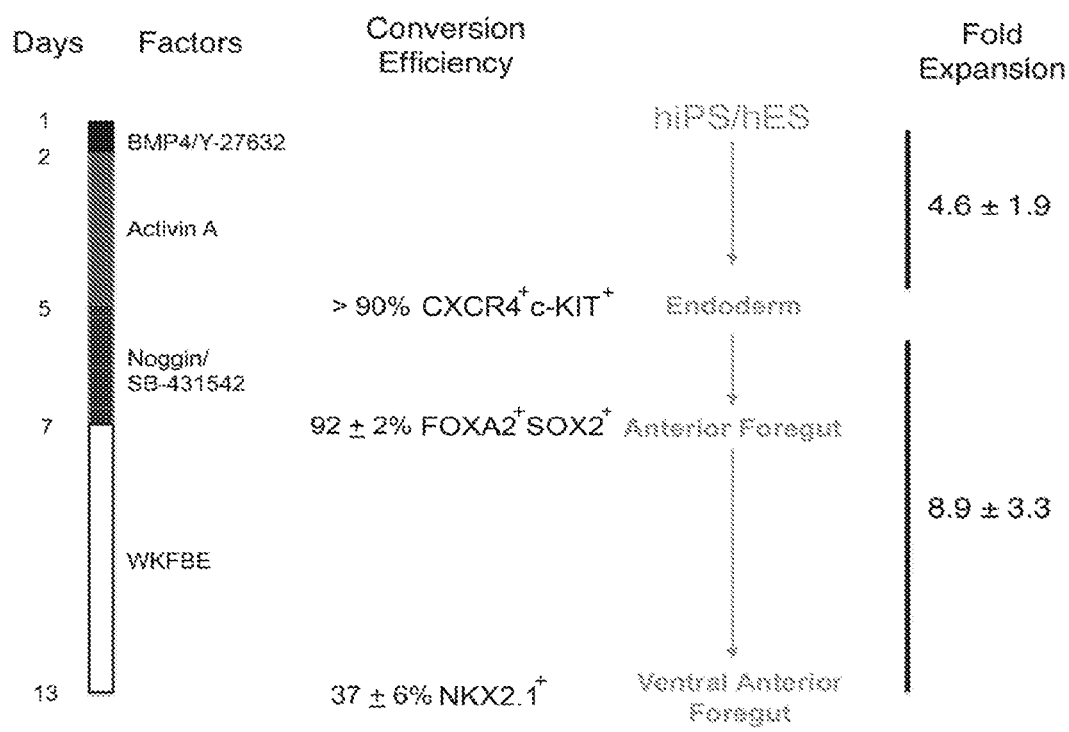
Figure 2D:
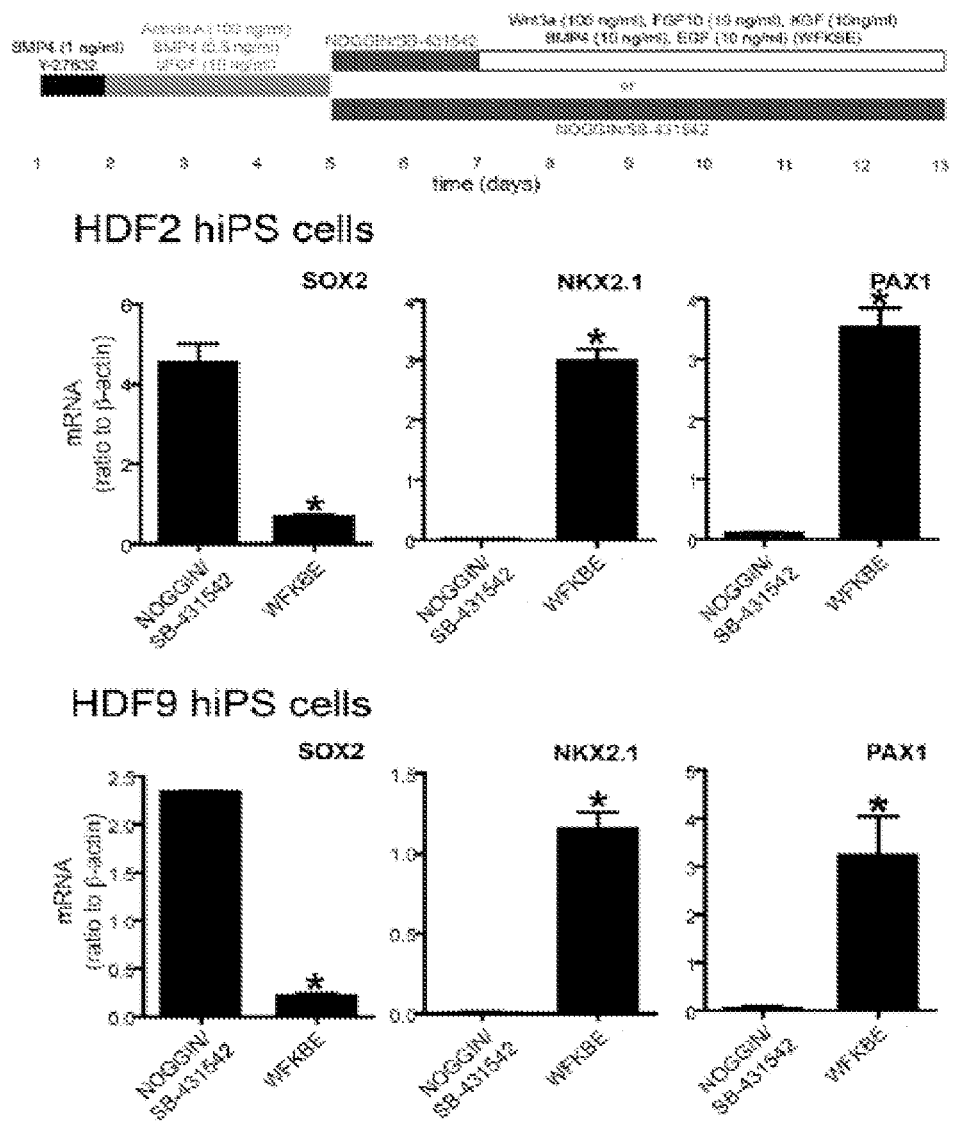
FIGS. 2d-e demonstrate the function of AFE generated from hES and hIPS cells. (2d) Expression of SOX1, NKX2.1, and PAX1 mRNA in HDF2 (upper) and HFD9 (lower) hiPS cells differentiated into AFE the conditions schematically represented on top of the panel (n=4 to 6 culture wells from 2 independent experiments, *significantly different from NOGGIN/SB-431542 conditions). (2e) Expression of EPCAM in HES2 cells differentiated into putative ventral AFE using NOGGIN/SB-431542 followed by WKFBE (left peak: isotype control, right peak: EPCAM).
Figure 2E:
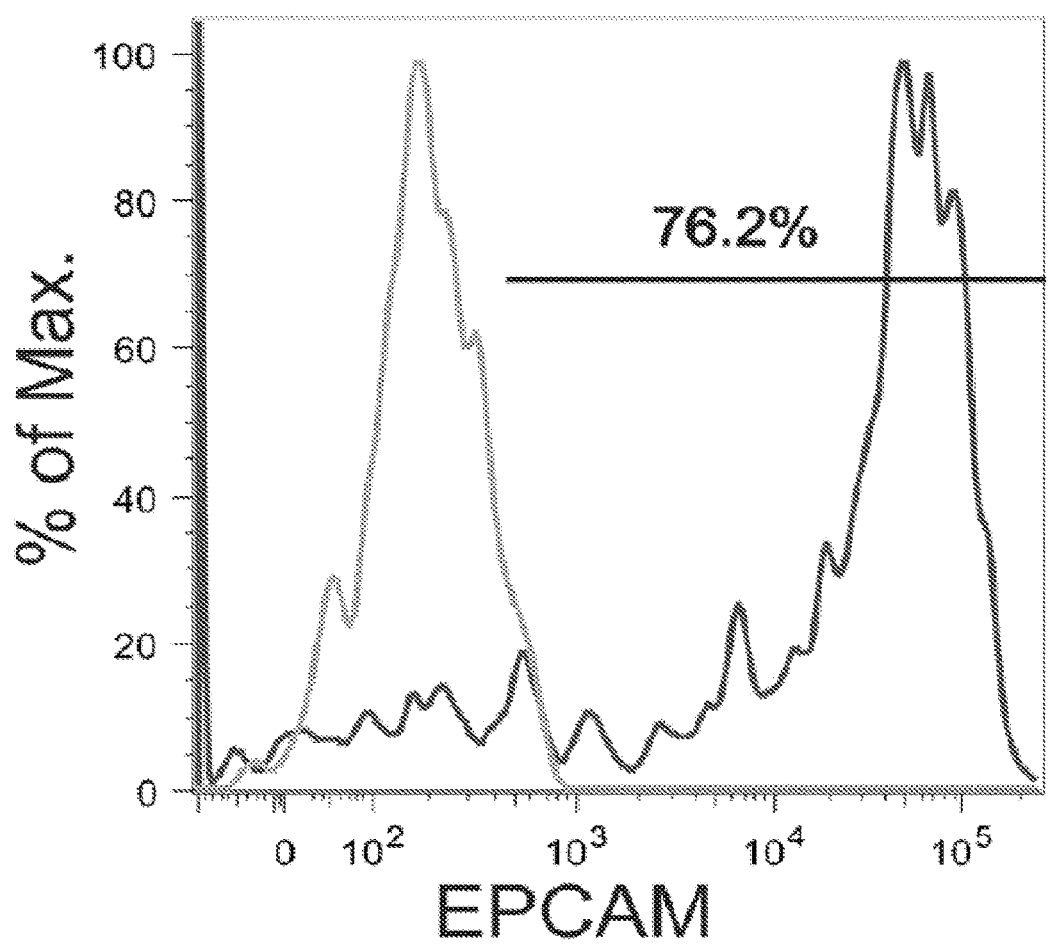

(2008); Morrisey & Hogan, Dev. Cell 18, 8-23 (2010)). At this stage, SOX2 expression remains higher dorsally, whereas NKX2.1 (lung and thyroid field (Zorn & Wells, Annu. Rev. Cell Dev. Biol. 25, 221-251 (2009); Morrisey & Hogan, Dev. Cell 18, 8-23 (2010))), NKX2.5 (transiently expressed in the ventral pharyngeal endoderm (Tanaka et al., Mol. Cell. Biol. 21, 4391-4398 (2001))) and PAX1 (within endoderm specifically expressed in the pharyngeal pouches (Wallin et al., Development 122, 23-30 (1996))) are specific ventral markers. Extended treatment with NOGGIN/SB-431542 until day 13 resulted in continued expression of SOX2, suggestive of a dorsal fate (FIG. 2a) and consistent with the fact that Noggin is expressed dorsally in the AFE, whereas BMP4 is expressed ventrally (Morrisey & Hogan, Dev. Cell 18, 8-23 (2010)). In contrast, replacing NOGGIN/SB-431542 with WNT3a, KGF, FGF10, BMP4 and EGF (all factors, WKFBE) at day 7 of culture resulted in lower expression of SOX2 and induced the ventral markers NKX2.1, PAX1 and NKX2.5 at day 13 (FIG. 2a for HES cells and FIG. 2d for HDF2 and HDF9 hiPS cells). Expression of the early thyroid marker, PAX8, was not observed, however, suggesting that NKX2.1 induction is indicative of commitment to a lung, rather than a thyroid, fate. Furthermore, P63, a marker of airway progenitor cells (Morrisey & Hogan, Dev. Cell 18, 8-23 (2010)), was strongly induced (FIG. 2a), and the vast majority of the cells expressed the epithelial marker EPCAM (FIG. 2e). Addition of individual factors was not sufficient for this transcriptional induction. Furthermore, only prior exposure to NOGGIN/SB-431542, and not to the hepatic cocktail or to media alone enabled subsequent upregulation of PAX1, NKX2.1 and NKX2.5 by WKFBE (FIG. 2b), demonstrating that NOGGIN/SB-431542 treatment of activin A-induced definitive endoderm is required for differentiation toward a ventral AFE fate. Timing of the WKFBE ventralization stimulus was critical, as only cultures treated at day 7, but not at day 9, were competent to express NKX2.1, PAX1 and NKX2.5. At this time, 92±2% of the cells were FOXA2+SOXA2+(FIG. 2c). Immunofluorescence revealed that after induction in WKFBE, 37±6% of cells expressed NKX2.1. During NOGGIN/SB-431542 followed by WKFBE treatment of activin A-induced endoderm, cells expanded an additional 8.95-+3.3-fold (FIG. 2c). Thus, NOGGIN/SB-431542-induced AFE is uniquely competent to respond to ventralization signals in vitro.

Figure 3A:
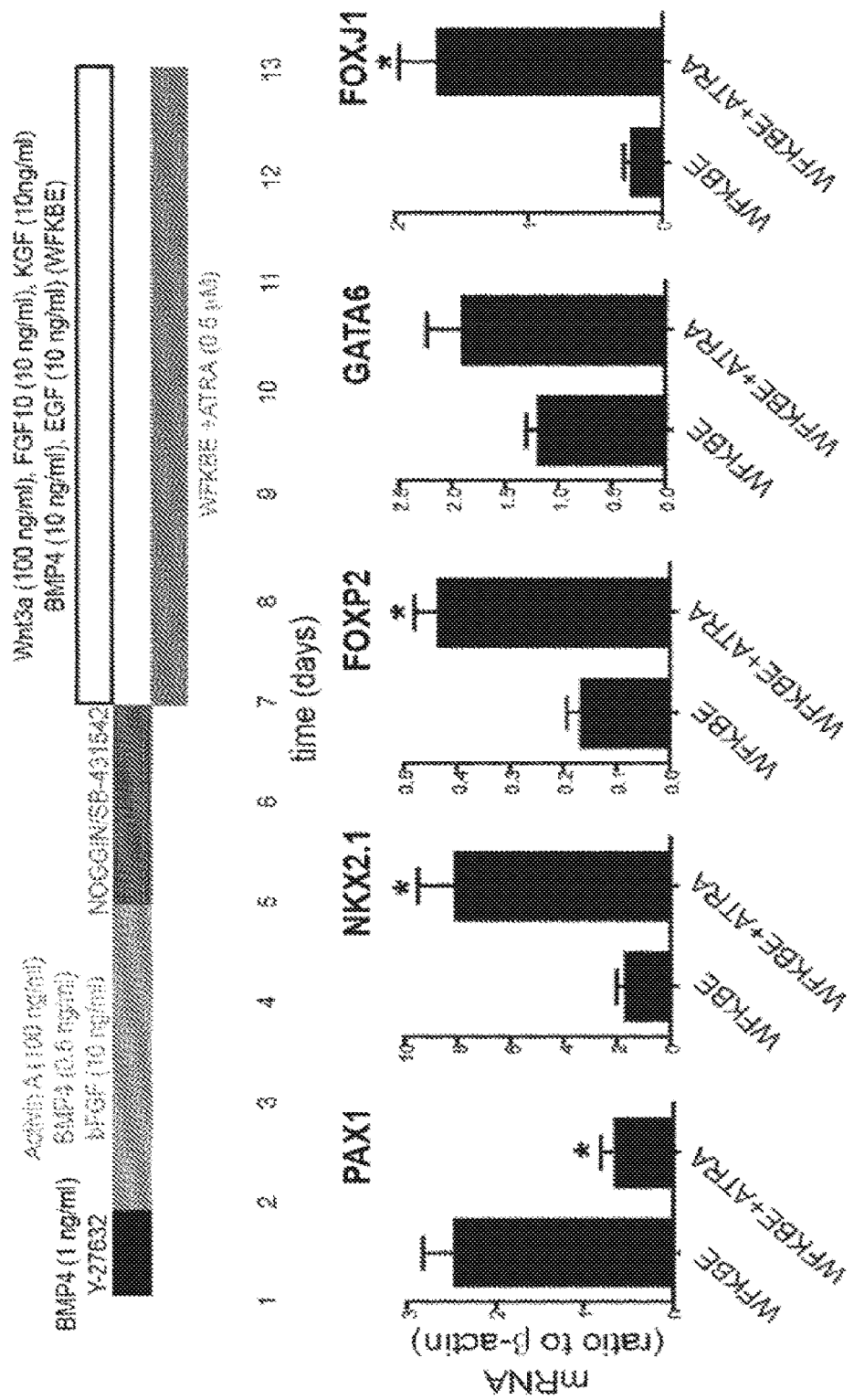
FIGS. 3a-b show induction of lung and pharyngeal pouch markers from ventral AFE generated in vitro. (3a) Expression of PAX1, NKX2.1, FOXP2, GATA6 and FOXJ1 in HES2-derived cells generated in the two conditions schematically represented on top of the panel (n=4 to six culture wells from three independent experiments, *, significantly different from WKFBE conditions; P<0.05). WKFBE: WNT3a, KGF, FGF10, BMP4 and EGF. (3b) Induction of SFTPC and GCM2 mRNA in ventralized AFE in the presence of factors indicated in the figure.
Figure 3B:
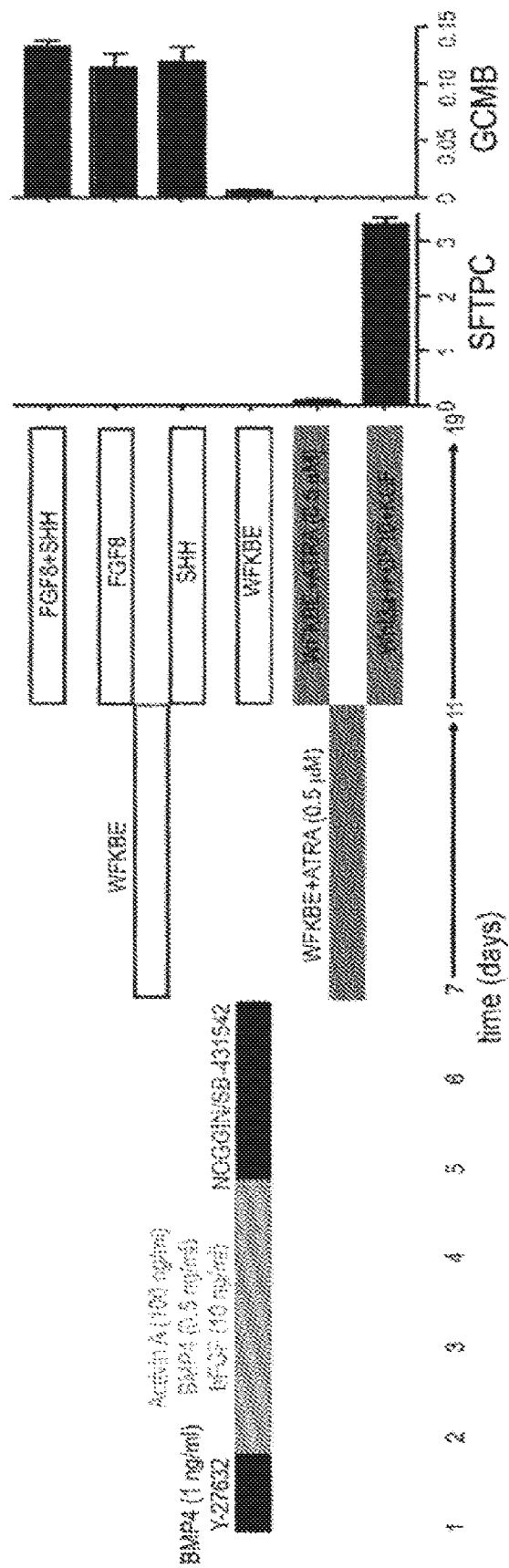

Exposure of NOGGIN/SB-431542-induced AFE to WKFBE did not result in expression of terminal differentiation markers for thymus, parathyroid, thyroid or lung at day 13 or day 19 of culture. As these cells had the potential to give rise to SFTPC+ cells in vivo, it was attempted to achieve lung specification in vitro. Consistent with a critical role for retinoic acid in early lung development (Chen et al., J. Clin. Invest. 120, 2040-2048 (2010)), addition of retinoic acid to the WKFBE cocktail decreased the expression of the pharyngeal pouch marker PAX1, but increased FOXP2, NKX2.1, GATA6 and FOXJ1, a constellation of markers suggestive of a lung fate (Morrisey & Hogan, Dev. Cell 18, 8-23 (2010)) (FIG. 3a). To enhance SFTPC induction, combinations of signaling agonists and antagonists were added at day 11 to AFE ventralized in the presence of retinoic acid. Among the >400 combinations examined, WNT3a+FGF10+FGF7 induced high levels of SFTPC mRNA (FIG. 3b) at day 19, consistent with the developmental observations that FGF10 and Wnt signaling are critical for distal lung development (Morrisey & Hogan, Dev. Cell 18, 8-23 (2010)). To assess whether NOGGIN/SB-431542-induced AFE could generate pharyngeal pouch derivatives, it was attempted to pattern the cultures ventralized with WKFBE in the absence of retinoic acid. Consistent with the requirement of sonic hedgehog (SHH) and FGF8 for parathyroid development (Moore-Scott & Manley, Dev. Biol. 278, 323-335 (2005)), addition of FGF8 or SHH to AFE cultures induced the parathyroid-specific marker GCM2 (FIG. 3b). The effects of SHH and FGF8 were not additive, mirroring in vivo epistasis studies showing that Shh is upstream of Fgf8 in mouse pharyngeal pouch development (Moore-Scott & Manley, Dev. Biol. 278, 323-335 (2005)). Although not all temporal and signaling permutations were tested exhaustively, these data suggest that NOGGIN/SB-431542-induced cells are capable of differentiating into downstream lineages, including the lung field and pharyngeal pouches.

Collectively, the data show that dual inhibition of BMP and TGF-β signaling in hES/hiPS cell-derived definitive endoderm specifies a highly enriched AFE population, providing an in vitro approach for the directed differentiation of human pluripotent cells into cell types and tissues derived from the AFE in vivo.

REFERENCES

1. Cai et al., Hepatology 45, 1229-1239 (2007).
2. Murry & Keller, Cell 132, 661-680 (2008).
3. Yamanaka, Cell 137, 13-17 (2009).
4. Jenq & van den Brink, Nat. Rev. Cancer 10, 213-221 (2010).
5. Lai & Jin, Stem Cells 27, 3012-3020 (2009).
6. Hidaka et al., Stem Cells Dev. 19, 1735-1743 (2010).
7. Lin et al., Endocrinology 144, 2644-2649 (2003).
8. Bingham et al., Stem Cells Dev. 18, 1071-1080 (2009).
9. Wang et al., Proc. Natl. Acad. Sci. USA 104, 4449-4454 (2007).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing an enriched population of anterior foregut endoderm cells from pluripotent cells, the method comprising:
   (i) culturing isolated mammalian pluripotent cells under conditions that induce the pluripotent cells to form definitive endoderm cells; and
   (ii) culturing the definitive endoderm cells in the presence of an inhibitor of a bone morphogenetic protein ("BMP") and an inhibitor of a transforming growth factor beta ("TGF-β") such that definitive endoderm cells form anterior foregut endoderm cells.

2. The method of claim 1, wherein the pluripotent cells are cultured in the presence of basic fibroblast growth factor ("bFGF"), bone morphogenetic protein ("BMP") and Activin A to induce said pluripotent cells to form said definitive endoderm cells.

3. The method of claim 1, wherein the definitive endoderm cells are cultured in the absence of Activin A.

4. The method of claim 1, wherein said inhibitor of bone morphogenetic protein ("BMP") is Noggin or Chordin.

5. The method of claim 4, wherein said inhibitor of bone morphogenetic protein ("BMP") is Noggin.

6. The method of claim 1, wherein the inhibitor of transforming growth factor beta ("TGF-beta") signaling is SB-431542.

7. The method of claim 1, wherein the pluripotent cells are cultured for 1-4 days.

8. The method of claim 1, wherein the definitive endoderm cells are cells are cultured for 2-6 days.

9. The method of claim 1, further comprising isolating said anterior foregut endoderm cells.

10. The method of claim 1, wherein the pluripotent cells are ES cells.

11. The method of claim 1, wherein the pluripotent cells are iPS cells.

12. The method of claim 11, wherein the pluripotent cells are human cells.

13. The method of claim 1, wherein the definitive endoderm cell is an embryoid body cell.

* * * * *